United States Patent
Tashiro

(10) Patent No.: US 10,743,771 B2
(45) Date of Patent: Aug. 18, 2020

(54) PHOTOACOUSTIC IMAGE GENERATION APPARATUS

(71) Applicant: FUJIFILM Corporation, Tokyo (JP)

(72) Inventor: Rika Tashiro, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 821 days.

(21) Appl. No.: 15/464,904

(22) Filed: Mar. 21, 2017

(65) Prior Publication Data
US 2017/0188839 A1 Jul. 6, 2017

Related U.S. Application Data

(63) Continuation of application No. PCT/JP2015/004862, filed on Sep. 24, 2015.

(30) Foreign Application Priority Data

Sep. 25, 2014 (JP) .................................. 2014-194809

(51) Int. Cl.
*A61B 5/00* (2006.01)
*A61B 5/06* (2006.01)
*A61B 1/00* (2006.01)

(52) U.S. Cl.
CPC .............. *A61B 5/0095* (2013.01); *A61B 1/00* (2013.01); *A61B 5/742* (2013.01); *A61B 5/061* (2013.01); *A61B 5/6848* (2013.01); *A61B 2576/00* (2013.01)

(58) Field of Classification Search
CPC ....... A61B 5/0095; A61B 5/742; A61B 5/061; A61B 5/6848; A61B 1/00; A61B 2576/00
See application file for complete search history.

(56) References Cited

U.S. PATENT DOCUMENTS

| 2010/0174197 A1 | 7/2010 | Nakajima et al. |
| 2012/0078103 A1 | 3/2012 | Tashiro et al. |
| 2014/0155739 A1 | 6/2014 | Manohar |
| 2015/0297092 A1 | 10/2015 | Irisawa |
| 2016/0270667 A1 | 9/2016 | Nakajima et al. |

FOREIGN PATENT DOCUMENTS

| JP | 2009-31262 A | 2/2009 |
| JP | 2012-120747 A | 6/2012 |
| JP | 2012-143389 A | 8/2012 |
| JP | 2013-13713 A | 1/2013 |
| WO | WO 2014/109148 A1 | 7/2014 |

OTHER PUBLICATIONS

International Search Report, issued in PCT/JP2015/004862 (PCT/ISA/210), dated Jan. 26, 2016.
Written Opinion of the International Searching Authority, issued in PCT/JP2015/004862 (PCT/ISA/237), dated Jan. 26, 2016.

*Primary Examiner* — Boniface N Nganga
(74) *Attorney, Agent, or Firm* — Birch, Stewart, Kolasch & Birch, LLP

(57) ABSTRACT

An insertion needle includes an outer needle and an inner needle, and the inner needle includes a light emitting portion and a photoacoustic wave generating portion. An insertion and removal detection unit detects that the inner needle of the insertion needle has been removed from the outer needle. In a case where it is detected that the inner needle has been removed, a processing switching unit changes the image display so as to be different from the image display before it is detected that the inner needle has been removed.

17 Claims, 12 Drawing Sheets

PHOTOACOUSTIC IMAGE GENERATION APPARATUS

CROSS REFERENCE TO RELATED APPLICATIONS

The present application is a Continuation of PCT International Application No. PCT/JP2015/004862 filed on Sep. 24, 2015, which claims priority under 35 U.S.C. § 119(a) to Japanese Patent Application No. 2014-194809 filed on Sep. 25, 2014. Each of the above applications is hereby expressly incorporated by reference, in its entirety, into the present application.

BACKGROUND OF THE INVENTION

1. Field of the Invention

The present invention relates to a photoacoustic image generation apparatus, more specifically, to a photoacoustic image generation apparatus for generating a photoacoustic image by detecting photoacoustic waves generated in a subject after emitting light to the subject.

2. Description of the Related Art

As a kind of image examination method capable of examining the state of the inside of a living body in a non-invasive manner, an ultrasound examination method is known. In ultrasound examination, an ultrasound probe capable of transmitting and receiving ultrasound waves is used. When ultrasound waves are transmitted to the subject (living body) from the ultrasound probe, the ultrasound waves propagate through the living body to be reflected on the tissue interface. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of the living body using the photoacoustic effect is known. In general, in photoacoustic imaging, pulsed laser light, such as a laser pulse, is emitted into the body. In the living body, a living tissue absorbs the energy of the pulsed laser light, and ultrasound waves (photoacoustic waves) due to adiabatic expansion due to the energy are generated. By detecting the photoacoustic waves using an ultrasound probe or the like and forming a photoacoustic image based on the detection signal, it is possible to visualize the inside of the living body based on the photoacoustic waves.

For photoacoustic imaging, JP2009-31262A discloses a combination of photoacoustic imaging and treatment using an insertion needle. In JP2009-31262A, an affected part such as a tumor, a part suspected to be an affected part, or the like is found by generating a photoacoustic image and observing the image. In order to examine such a part more precisely or in order to perform injection into the affected part, sampling of cells, injection into the affected part, and the like are performed using an insertion needle, such as an injection needle or a cytodiagnosis needle. In JP2009-31262A, it is possible to perform insertion while observing the affected part using a photoacoustic image.

In addition, JP2013-13713A also discloses a combination of photoacoustic imaging and an insertion needle. In JP2013-13713A, the insertion needle has a light emitting portion. Light emitted from a laser light source is guided to the light emitting portion of the insertion needle using, for example, an optical fiber, and is emitted to the outside from the light emitting portion. By detecting photoacoustic waves, which are generated by absorbing the light emitted from the light emitting portion of the insertion needle, using an ultrasound probe and generating a photoacoustic image based on the detection signal, it is possible to check the position of the insertion needle.

Here, the success of the brachial plexus block is largely based on the localization of the nerve, the position of a needle, and an appropriate technique for local anesthetic injection. In recent years, nerve block injection is performed by inserting an insertion needle while observing an ultrasound image. However, there is a problem that it is difficult for the insertion needle to be visually recognized only with the ultrasound image. In the insertion, it is important that the entire needle can be seen. However, in order to prevent pneumothorax and the like, it is most important to check the position of the distal end of the needle. In photoacoustic imaging, usually, emission of light to the subject is performed from the surface of the subject. In particular, when the distal end of the insertion needle is inserted up to a deep position (for example, a position deeper than 3 cm from the subject surface), light emitted from the subject surface does not sufficiently reach the insertion needle that has been inserted to the deep position. Accordingly, it is difficult to check the position of the distal end of the insertion needle in a photoacoustic image.

To solve the problem, there is a technique disclosed in WO2014/109148A. In WO2014/109148A, light emitted from the light source is guided to the vicinity of the distal end of the insertion needle using an optical fiber or the like, and the light is emitted to a photoacoustic wave generating portion of the insertion needle from there. In this manner, it is possible to check the position using a photoacoustic image even when the insertion needle is inserted up to a deep position. WO2014/109148A also discloses that the insertion needle includes an outer needle and an inner needle inserted into the inner cavity of the outer needle, an optical fiber is inserted into the inner needle, and a photoacoustic wave generating portion is provided in a distal end portion of the inner needle.

SUMMARY OF THE INVENTION

In WO2014/109148A, however, since the optical fiber is included in the inner needle, it is not possible to emit light to the photoacoustic wave generating portion if the inner needle is removed from the outer needle when injecting an anesthetic or the like. Accordingly, it is not possible to generate a photoacoustic wave in the distal end portion of the insertion needle. As a result, since it is not possible to check the position of the insertion needle using the photoacoustic image, the visibility of the needle tip returns to the same level as the visibility in a normal ultrasound image.

In view of the above, it is an object of the present invention to provide a photoacoustic image generation apparatus capable of checking the position of an insertion needle even if an inner needle is removed from an outer needle in a case where the insertion needle includes the outer needle and the inner needle and the inner needle includes an optical fiber.

In order to achieve the aforementioned object, there is provided a photoacoustic image generation apparatus comprising: an insertion needle that has an outer needle having an inner cavity and an inner needle removably inserted into the inner cavity of the outer needle, the inner needle including a light emitting portion that emits light guided from a light source and a photoacoustic wave generating portion that absorbs the light emitted from the light emitting portion to generate photoacoustic waves; acoustic wave detection means for detecting the photoacoustic waves emitted from the photoacoustic wave generating portion; photoacoustic image generation means for generating a photoacoustic image based on the detected photoacoustic waves; image output means for displaying the photoacoustic image on image display means; insertion and removal detection means for detecting that the inner needle has been removed from the outer needle; and processing switching means for changing image display so as to be different from image display before it is detected that the inner needle has been removed in a case where it is detected that the inner needle has been removed.

In the present invention, it is preferable that the insertion needle is inserted into a subject in a state in which the inner needle has been inserted into the outer needle.

It is preferable that the processing switching means changes a display color of the photoacoustic image displayed on the image display means before and after it is detected that the inner needle has been removed.

The photoacoustic image generation apparatus of the present invention can further comprise sound source position detection means for detecting a position of a generation source of the photoacoustic waves in the insertion needle based on the photoacoustic image. In this case, the image output means may display a marker indicating the detected position of the generation source of the photoacoustic waves on the image display means. The processing switching means may change a display color of the marker displayed on the image display means before and after it is detected that the inner needle has been removed.

In the photoacoustic image generation apparatus of the present invention, the acoustic wave detection means may further detect reflected acoustic waves of acoustic waves transmitted into a subject. In this case, the photoacoustic image generation apparatus can further comprise reflected acoustic wave image generation means for generating a reflected acoustic wave image based on the detected reflected acoustic waves.

The image output means may display an image, in which the photoacoustic image is superimposed on the reflected acoustic wave image, on the image display means before it is detected that the inner needle has been removed, and display the reflected acoustic wave image on the image display means after it is detected that the inner needle has been removed.

The image output means may display an image, in which a photoacoustic image generated before it is detected that the inner needle has been removed is superimposed on the reflected acoustic wave image, on the image display means after it is detected that the inner needle has been removed.

The photoacoustic image generation apparatus of the present invention can adopt a configuration further having movement detection means for detecting a movement of the insertion needle based on a reflected acoustic wave image at a time before it is detected that the inner needle has been removed and a reflected acoustic wave image at a current time after it is detected that the inner needle has been removed.

In the above, the movement detection means may detect a movement of a needle tip of the insertion needle based on a difference between a total value of pixel values in the reflected acoustic wave image at the time before it is detected that the inner needle has been removed and a total value of pixel values in the reflected acoustic wave image at the current time.

The movement detection means may calculate the total values of the pixel values after performing distal end emphasis processing, which is for emphasizing a distal end portion of the insertion needle, for each of the reflected acoustic wave image at the time before it is detected that the inner needle has been removed and the reflected acoustic wave image at the current time.

It is preferable that the movement detection means calculates a total value of pixel values in a region including a position of the photoacoustic wave generating portion in the photoacoustic image.

The photoacoustic image generation apparatus of the present invention can further comprise warning means for warning a user in a case where an amount of movement detected by the movement detection means is equal to or greater than a threshold value.

When an amount of movement detected by the movement detection means is equal to or greater than a threshold value, the image output means may change a display color of the photoacoustic image to a different display color from a display color before the amount of movement detected by the movement detection means reaches the threshold value or more.

When the amount of movement detected by the movement detection means becomes smaller than the threshold value after the amount of movement reaches the threshold value or more, the image output means may return the display color of the photoacoustic image to the display color before the amount of movement reaches the threshold value or more.

The photoacoustic image generation apparatus of the present invention needle can further comprise needle distal end extraction means for extracting a distal end candidate of the insertion needle from the reflected acoustic image. In this case, the image output means may display a marker, which indicates a position of a distal end candidate of the insertion needle extracted by the needle tip candidate extraction means, on the image display means in a case where an amount of movement detected by the movement detection means is equal to or greater than a threshold value.

The image output means may stop the display of the marker when the amount of movement detected by the movement detection means becomes smaller than the threshold value after the amount of movement reaches the threshold value or more.

The needle tip candidate extraction means may end the needle tip candidate extraction processing in a case where the movement detection means detects that the insertion needle has moved by a predetermined amount or more in a direction in which the insertion needle is removed.

In the photoacoustic image generation apparatus of the present invention, in a case where the insertion needle includes an outer needle and an inner needle and the inner needle includes an optical fiber, it is possible to check the position of the insertion needle even if the inner needle is removed from the outer needle.

DESCRIPTION OF THE PREFERRED EMBODIMENTS

Figure 1:
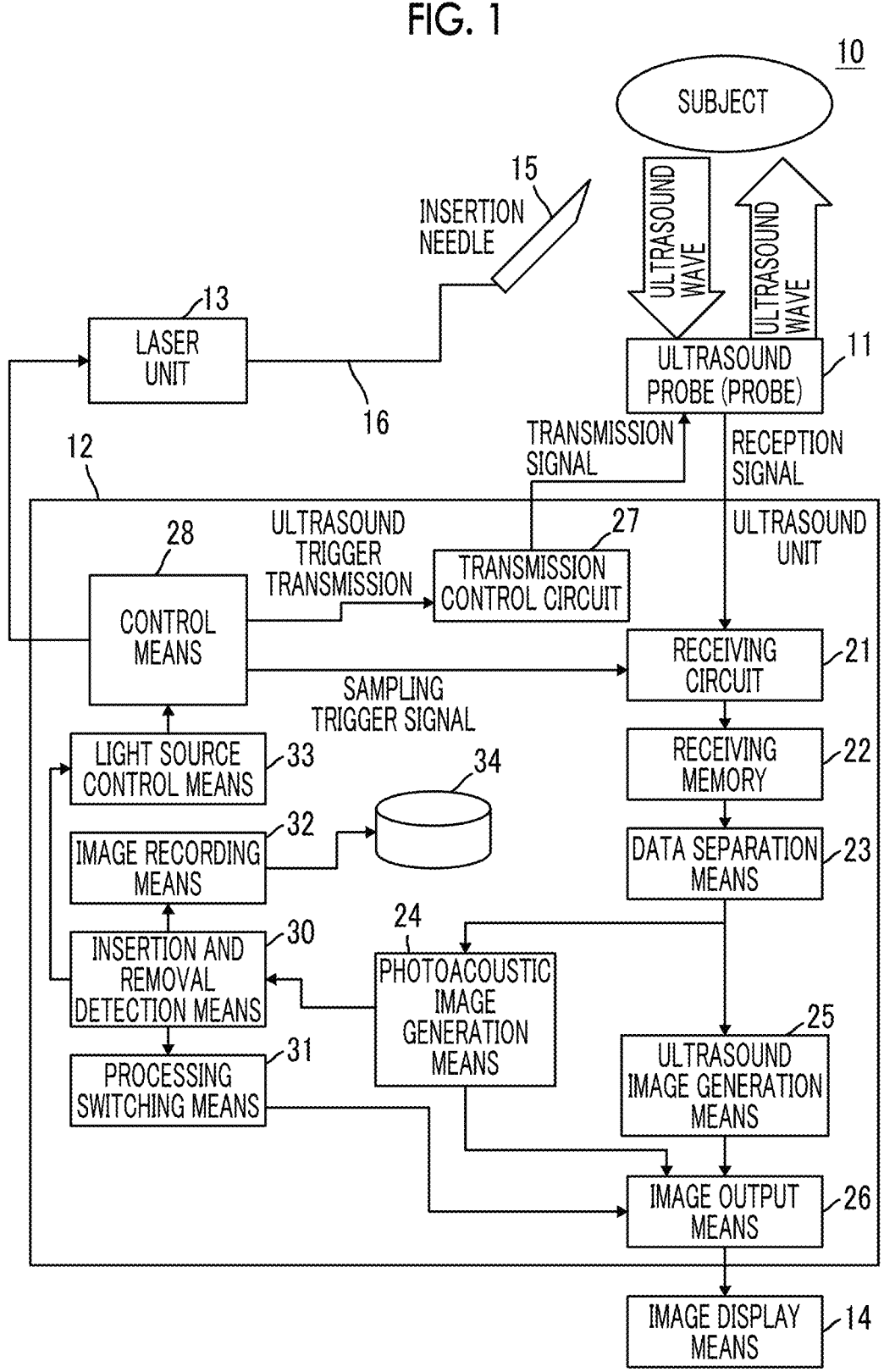
FIG. 1 is a block diagram showing a photoacoustic image generation apparatus according to a first embodiment of the present invention.

Hereinafter, embodiments of the present invention will be described in detail with reference to the diagrams. FIG. 1 shows a photoacoustic image generation apparatus according to a first embodiment of the present invention. A photoacoustic image generation apparatus 10 includes a probe (ultrasound probe) 11, an ultrasound unit 12, a laser unit 13, and an insertion needle 15. In the embodiment of the present invention, an ultrasound wave is used as an acoustic wave. However, the present invention is not limited to the ultrasound wave, and an acoustic wave having an audible frequency may be used as long as an appropriate frequency can be selected according to an examination target, measurement conditions, or the like.

The laser unit 13 is a light source. Light emitted from the laser unit 13 is guided to the insertion needle 15, for example, using light guide means, such as an optical fiber 16. The laser unit 13 is, for example, a solid state laser light source using an yttrium aluminum garnet (YAG), alexandrite, or the like. Types of light sources are not particularly limited, and the laser unit 13 may be a laser diode light source (semiconductor laser light source), or may be an optical amplification type laser light source using a laser diode light source as a seed light source. Light sources other than the laser light source may be used.

Figure 2:
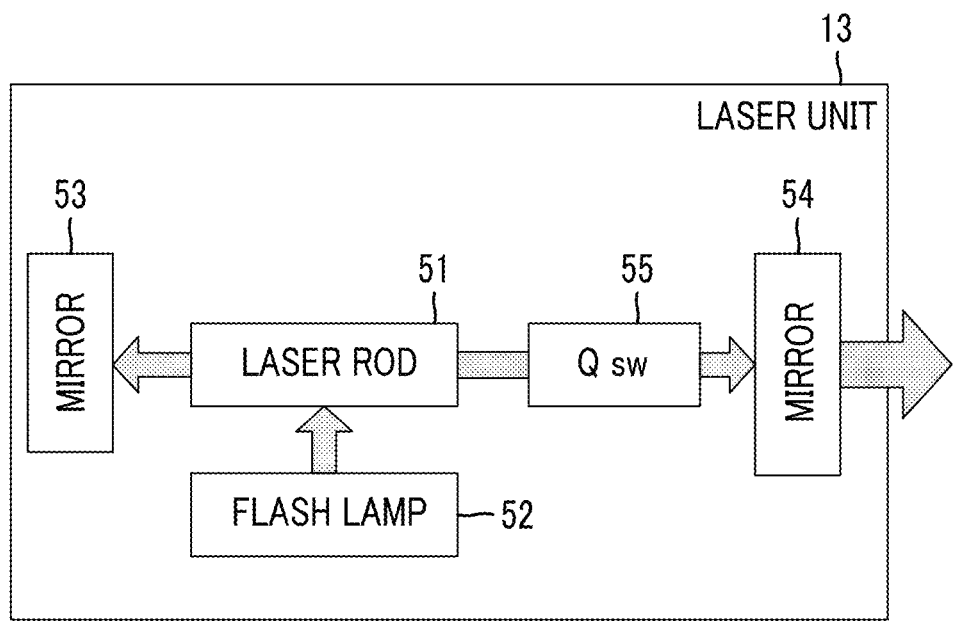
FIG. 2 is a block diagram showing an example of the configuration of a laser unit.

FIG. 2 shows an example of the configuration of the laser unit 13. The laser unit 13 has a laser rod 51, a flash lamp 52, mirrors 53 and 54, and a Q switch 55. The laser rod 51 is a laser medium. As the laser rod 51, for example, alexandrite crystal can be used. The flash lamp 52 is an excitation light source, and emits excitation light to the laser rod 51. The excitation light source is not limited to the flash lamp 52, and light sources other than the flash lamp 52 may be used as the excitation light source.

The mirrors 53 and 54 face each other with the laser rod 51 interposed therebetween, and an optical resonator is formed by the mirrors 53 and 54. The mirror 54 is located on the output side. The Q switch 55 is inserted into the optical resonator. By quickly changing the insertion loss in the optical resonator from high loss (low Q) to low loss (high Q) using the Q switch 55, it is possible to obtain pulsed laser light. The pulsed laser light emitted from the mirror 54 on the output side of the laser unit 13 is guided to the insertion needle.

Referring back to FIG. 1, the insertion needle 15 is a needle inserted into the subject. The insertion needle 15 has an outer needle and an inner needle. The outer needle has an opening at the distal end formed at an acute angle, and has an inner cavity thereinside. The inner needle has an outer diameter of approximately the same size as the inner cavity of the outer needle, and is configured so as to be able to be inserted into or removed from the hollow outer needle. The inner needle is inserted into the inner cavity of the outer needle from the proximal end portion side of the outer needle, thereby sealing at least a part of the inner cavity of the outer needle to the extent that, for example, a cut piece of the living body or the like is prevented from entering the inner cavity. A protruding portion for connection alignment is provided in the proximal end portion of the inner needle, and a groove engaged with the protruding portion of the proximal end portion of the inner needle is provided in the proximal end portion of the outer needle. When setting the inner needle inside the outer needle, the proximal end portion of the inner needle is fitted to the proximal end portion of the outer needle after aligning the position of the protrusion of the proximal end portion of the inner needle and the position of the groove of the proximal end portion of the outer needle.

An operator, such as a doctor, inserts the insertion needle 15 into the subject in a state in which the inner needle is set inside the outer needle. Since the inner cavity of the outer needle is clogged with the inner needle, it is possible to prevent a piece of flesh or the like from entering the inner cavity while the needle is being inserted. Accordingly, it is possible to prevent the insertion feeling of the operator from being adversely affected. In addition, it is possible to prevent the inflow of water from the insertion part to the inner cavity of the outer needle. After the insertion into the subject, the operator releases the connection between the proximal end portion of the inner needle and the proximal end portion of the outer needle, and removes the inner needle from the outer needle. After removing the inner needle, for example, a syringe or the like is attached to the proximal end portion of the outer needle to inject a drug, such as an anesthetic.

Figure 3:
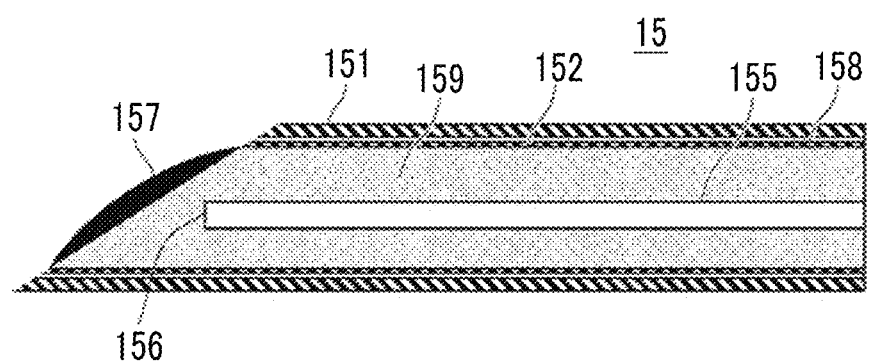
FIG. 3 is a cross-sectional view showing the vicinity of the distal end of an insertion needle.

FIG. 3 shows a cross section of the vicinity of the distal end of the insertion needle 15. The insertion needle 15 has an insertion needle body 151 forming the outer needle and an inner needle 152 inserted into the insertion needle body 151. The inner needle 152 includes a light guide member 155, a light absorption member 157, a tube 158, and a transparent resin 159. The tube 158 is a hollow tube formed of polyimide, for example. The tube 158 may be a metal tube formed of stainless steel. The outer diameter of the tube 158 is slightly smaller than the diameter of the inner cavity of the insertion needle body 151. The transparent resin 159 is disposed within the tube 158. For example, an epoxy resin (adhesive) is used as the transparent resin 159. The tube 158 and the transparent resin 159 are cut at an acute angle similar to the insertion needle tip formed at an acute angle. The transparent resin 159 may clog at least a distal end portion of the tube 158, and does not necessarily need to clog the entire inside of the tube 158. As the transparent resin 159, a photocurable resin, a thermally curable resin, or a room temperature curable resin can be used.

Light guided by the optical fiber 16 (refer to FIG. 1) is incident on the light guide member 155 in the inner needle 152 from the optical connector provided in the proximal end portion of the inner needle, for example. Instead of providing the optical connector in the proximal end portion of the inner needle, the optical fiber 16 may be inserted into the tube 158 and the optical fiber 16 itself may be used as the light guide member 155. The light guide member 155 guides the light emitted from the laser unit 13 in the vicinity of the opening of the insertion needle. The light guided by the light guide member 155 is emitted from a light emitting portion 156 provided in the vicinity of the opening. The light guide member 155 is formed of, for example, an optical fiber, and the end surface of the optical fiber on the light traveling side when viewed from the laser unit 13 forms the light emitting portion 156. For example, laser light of 0.2 mJ is emitted from the light emitting portion 156.

The light guide member 155 is embedded into the tube 158 by the transparent resin 159. The light absorption member 157 that is a photoacoustic wave generating portion is disposed at the distal end of the tube 158, and the light emitted from the light emitting portion 156 is emitted to the light absorption member 157. Due to the absorption of the emitted light by the light absorption member 157, photoacoustic waves are generated at the distal end of the insertion needle. Since the light absorption member 157 is present at the distal end of the insertion needle 15, it is possible to generate photoacoustic waves at one point of the distal end of the insertion needle 15. Since the length of a photoacoustic wave generation source (sound source) is sufficiently shorter than the length of the entire insertion needle, the sound source can be regarded as a point source. As the light absorption member 157, for example, an epoxy resin containing black pigment mixed thereinto, a polyurthane resin, a fluorine resin, or silicone rubber can be used. Alternatively, a metal or oxide having a light absorption property with respect to the wavelength of laser light may be used as the light absorption member 157. For example, oxides, such as an iron oxide, a chromium oxide, and a manganese oxide having a high light absorption property with respect to the wavelength of laser light, can be used as the light absorption member 157. Alternatively, a metal, such as Ti or Pt, may be used as the light absorption member 157.

The inner needle 152 can be manufactured in the following procedure. First, the transparent resin 159 before curing is injected into the tube 158. Then, the light guide member 155 is inserted into the tube 158, and is positioned such that the light emitting end of the light guide member 155 forming the light emitting portion 156 is disposed in the vicinity of the tube 158. In this positioning, the position may be adjusted such that the light emitting end is disposed at the distal end of the tube 158 by observing the light guide member 155 using a microscope, for example. Here, "vicinity" refers to a position where it is possible to generate photoacoustic waves capable of imaging the position of the distal end of the insertion needle 15 with accuracy, which is required for insertion work in the light absorption member 157 disposed at the distal end, in a case where the light emitting portion 156 is disposed at the position. For example, "vicinity" is the range of 0 mm to 3 mm toward the proximal end side from the distal end of the insertion needle 15. Since the transparent resin 159 is transparent, it is possible to check the position of the light emitting end of the light guide member 155 during adjustment. Instead of the above, the light guide member 155 may be inserted first, and the transparent resin 159 may be injected thereafter.

After positioning, the transparent resin 159 is cured by heat curing in a state in which the light guide member 155 has been inserted into the tube 158. Then, the distal ends of the tube 158 and the transparent resin 159 are cut at an acute angle so as to have a shape suitable for the distal end of the insertion needle body 151. Then, the resin having a light absorption property that forms the light absorption member 157 is applied to cover at least a part of the cut surface, and the resin is cured by heat curing, for example.

In the above, the light guide member 155 is inserted into the tube 158 and the position is adjusted, and the transparent resin is cured and is then cut at an acute angle. However, the invention is not limited thereto. The tube may be cut at an acute angle first, the light guide member 155 may be inserted into the tube and the position may be adjusted, and the transparent resin may be cured. In this case, a metal tube formed of stainless steel may be used as the tube.

Referring back to FIG. 1, a probe 11 is acoustic wave detection means, and has a plurality of detector elements (ultrasound transducers) arranged in a one-dimensional manner. The probe 11 detects photoacoustic waves generated from the light absorption member 157 (refer to FIG. 3) after the insertion needle 15 is inserted into the subject. In addition to the detection of photoacoustic waves, the probe 11 performs transmission of acoustic waves (ultrasound waves) to the subject and reception of reflected acoustic waves (reflected ultrasound waves) of the transmitted ultrasound waves. In addition, transmission and reception of ultrasound waves may be performed at separate positions. For example, ultrasound waves may be transmitted from a position different from the probe 11, and reflected ultrasound waves of the transmitted ultrasound waves may be received by the probe 11. The probe 11 is not limited to the linear probe, but may be a convex probe or a sector probe.

The ultrasound unit 12 has a receiving circuit 21, a receiving memory 22, data separation means 23, the photoacoustic image generation means 24, ultrasound image generation means 25, image output means 26, a transmission control circuit 27, control means 28, insertion and removal detection means 30, processing switching means 31, image recording means 32, light source control means 33, and a storage unit 34. The ultrasound unit 12 forms a signal processing device.

The receiving circuit 21 receives a detection signal output from the probe 11, and stores the received detection signal in the receiving memory 22. Typically, the receiving circuit 21 includes a low noise amplifier, a variable gain amplifier, a low pass filter, and an analog to digital converter (AD converter). The detection signal of the probe 11 is amplified by the low noise amplifier, and then the gain is adjusted according to the depth by the variable gain amplifier and a high-frequency component is cut by the low pass filter. Then, conversion into a digital signal is performed by the AD converter, and the digital signal is stored in the receiving memory 22. The receiving circuit 21 is formed by one integral circuit (IC), for example.

The probe 11 outputs a detection signal of photoacoustic waves and a detection signal of reflected ultrasound waves, and detection signals (sampling data) of photoacoustic waves and reflected ultrasound waves after AD conversion are stored in the receiving memory 22. The data separation means 23 reads the sampling data of the detection signal of photoacoustic waves from the receiving memory 22, and transmits the sampling data to the photoacoustic image generation means 24. In addition, the data separation means 23 reads the sampling data of reflected ultrasound waves from the receiving memory 22, and transmits the sampling data to the ultrasound image generation means (reflected acoustic wave image generation means) 25.

The photoacoustic image generation means 24 generates a photoacoustic image based on the detection signal of photoacoustic waves detected by the probe 11. The generation of a photoacoustic image includes, for example, image reconstruction such as phase matching addition, detection, and logarithmic conversion. The ultrasound image generation means 25 generates an ultrasound image (reflected acoustic wave image) based on the detection signal of reflected ultrasound waves detected by the probe 11. The generation of an ultrasound image also includes image reconstruction such as phase matching addition, detection, and logarithmic conversion.

The image output means 26 outputs the photoacoustic image and the ultrasound image to image display means 14, such as a display device. For example, the image output means 26 superimposes the photoacoustic image and the ultrasound image, and outputs the result to the image display means 14.

The control means 28 controls each unit in the ultrasound unit 12. For example, in the case of acquiring a photoacoustic image, the control means 28 transmits a trigger signal to the laser unit 13 so that the laser unit 13 emits laser light. In addition, the control means 28 controls the sampling start timing of photoacoustic waves by transmitting a sampling trigger signal to the receiving circuit 21 in response to the emission of the laser light. The area where photoacoustic waves are to be detected may be divided into a plurality of areas. In this case, emission of light to the subject and detection of photoacoustic waves are performed for each area.

In the case of acquiring an ultrasound image, the control means 28 transmits an ultrasound wave transmission trigger signal for giving an instruction to transmit ultrasound waves to the transmission control circuit 27. When the ultrasound wave transmission trigger signal is received, the transmission control circuit 27 makes the probe 11 transmit ultrasound waves. The probe 11 detects reflected ultrasound waves by performing a scan while shifting the acoustic line by one line at a time, for example. The control means 28 transmits a sampling trigger signal to the receiving circuit 21 according to the timing of ultrasound wave transmission, thereby starting the sampling of reflected ultrasound waves.

The insertion and removal detection means 30 detects that the inner needle of the insertion needle 15 has been removed from the outer needle. The insertion and removal detection means 30 determines whether or not the inner needle has been removed from the outer needle, for example, based on the amount of change between frames in the pixel value of a photoacoustic image generated in time series. For example, the insertion and removal detection means 30 calculates the amount of change in a pixel value between frames of a pixel corresponding to the position of the light absorption member 157 (refer to FIG. 3) in a photoacoustic image. The insertion and removal detection means 30 determines whether or not the inner needle has been removed from the outer needle based on the amount of change. The insertion and removal detection means 30 determines that the inner needle has been removed, for example, when the pixel value decreases abruptly and the state in which the pixel value has decreased continues for a predetermined time (for example, 1 second) or more.

The insertion and removal detection means 30 may calculate the total value of the pixel values of a plurality of pixels of a photoacoustic image, and determine whether or not the inner needle has been removed from the outer needle based on the amount of change in the total value. For example, the insertion and removal detection means 30 calculates the total value of the pixel values of pixels in a region including the position of the light absorption member 157 in a photoacoustic image, and calculate the amount of change between frames in the total value. The insertion and removal detection means 30 may determine that the inner needle has been removed, for example, when the total value of the pixel values decreases abruptly and the state in which the total value of the pixel values has decreased continues for a predetermined time (for example, 1 second) or more. A total value of all pixel values may be calculated instead of a region of a part of the photoacoustic image, and it may be determined that the inner needle has been removed based on the amount of change in the total value.

The image output means 26 outputs an image, in which the photoacoustic image is superimposed on the ultrasound image, to the image display means 14 before the insertion and removal detection means 30 detects that the inner needle has been removed, and outputs a reflected acoustic wave image to the image display means 14 after it is detected that the inner needle has been removed. After it is detected that the inner needle has been removed, the image output means 26 may display an image, in which a photoacoustic image generated at a time before it is detected that the inner needle has been removed is superimposed on the reflected acoustic wave image, on the image display means 14.

When the insertion and removal detection means 30 detects that the inner needle has been removed, the processing switching means 31 changes the image display, which is displayed on the image display means 14, so as to be different from the image display before it is detected that the inner needle has been removed. The processing switching means 31 changes the display color of a photoacoustic image displayed on the image display means 14, for example, before and after it is detected that the inner needle has been removed.

When the insertion and removal detection means 30 detects that the inner needle has been removed, the image recording means 32 records an ultrasound image in the storage unit (recording medium) 34. For example, the storage unit 34 is a storage medium, such as a hard disk drive or a semiconductor memory. The image recording means 32 starts the recording of an ultrasound image, for example, after a predetermined time has passed from the time when it is detected that the inner needle has been removed. At this time, the image output means 26 may display, on the image display means 14, a remaining time until the image recording means 32 starts the recording of an ultrasound image after it is detected that the inner needle has been removed. The storage unit 34 does not necessarily need to be present inside the ultrasound unit 12, and may be present outside the ultrasound unit 12.

When the insertion and removal detection means 30 detects that the inner needle has been removed, the light source control means 33 suppresses the light emission of the laser unit 13, for example, through the control means 28. In order to suppress the light emission, in addition to stopping light emission, increasing the repetition period of light emission, reducing the light emission intensity, and the like are included. The light source control means 33 suppresses the light emission of the laser unit 13, for example, by suppressing the light emission of the flash lamp 52 (refer to FIG. 2). The suppression of light emission of the flash lamp 52 can be realized, for example, by turning off the power of a driving circuit for driving the flash lamp 52. In addition, the suppression of light emission of the flash lamp 52 can be realized by outputting no flash lamp trigger signal from the control means 28 or by masking the flash lamp trigger signal output from the control means 28.

Instead of the above, the light source control means 33 may suppress the light emission of the laser unit 13 by controlling the operation of the Q switch 55. The suppression of the operation of the Q switch 55 can be realized, for example, by turning off the power of a driving circuit for driving the Q switch 55. In addition, the suppression of the operation of the Q switch 55 can be realized by outputting no Q switch trigger signal from the control means 28 or by masking the Q switch trigger signal output from the control means 28. In a case where the laser unit 13 is a laser diode light source, the light source control means 33 may suppress the light emission of the light source by suppressing the driving of the laser diode. When it is detected that the inner needle has been inserted after it is detected that the inner needle has been removed, the light source control means 33 may release the suppression of light emission of the light source.

Although the case where the insertion and removal detection means 30 determines whether or not the inner needle has been removed from the outer needle based on the photoacoustic image has been described above, the present invention is not limited thereto. For example, an insertion and removal sensor may be provided in the insertion needle 15, and the insertion and removal detection means 30 may determine whether or not the inner needle has been removed from the outer needle based on the detection signal of the insertion and removal sensor. For example, as an insertion and removal sensor, a contact sensor is provided in a connection portion between the proximal end portion of the inner needle and the proximal end portion of the outer needle of the insertion needle 15. The contact sensor outputs a signal according to whether or not the proximal end portion of the inner needle and the proximal end portion of the outer needle are in contact with each other. For example, the contact sensor is in a conduction state when the proximal end portion of the inner needle and the proximal end portion of the outer needle are in contact with each other, and is in a non-conduction state when the proximal end portion of the inner needle and the proximal end portion of the outer needle are not in contact with each other. In this case, the insertion and removal detection means 30 can determine whether or not the inner needle has been removed from the outer needle according to whether or not terminals of the contact sensor are electrically connected to each other.

The insertion and removal sensor is not limited to the contact sensor. For example, the insertion and removal sensor may be configured to include a first electrode provided in the proximal end portion of the inner needle and a second electrode provided in the proximal end portion of the outer needle. The second electrode is electrically connected to the first electrode when the inner needle is correctly inserted into the outer needle. A signal indicating whether or not the first and second electrodes are electrically connected may be output from the insertion and removal sensor, and the insertion and removal detection means 30 may determine whether or not the inner needle has been removed based on the detection signal of the insertion and removal sensor.

Figure 4:
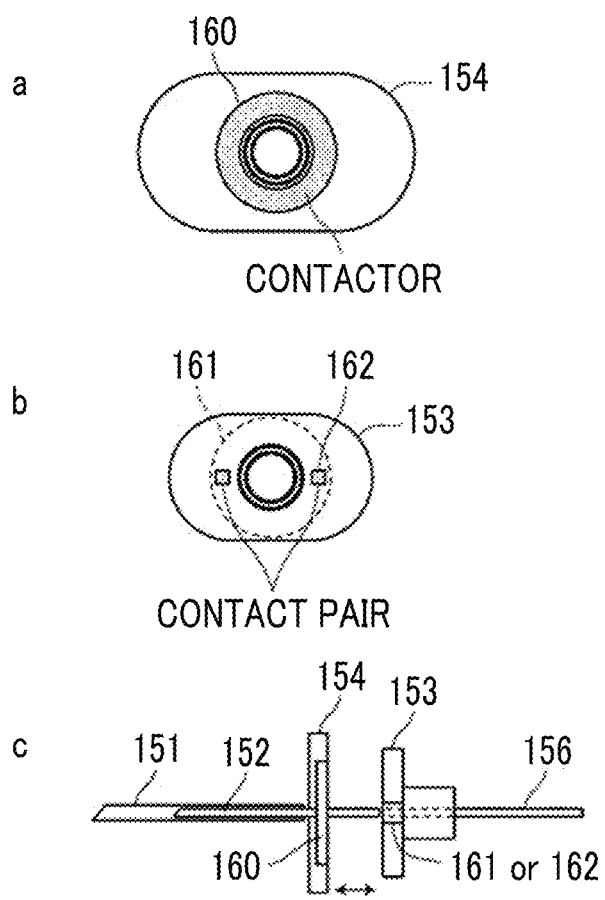
FIG. 4 is a diagram showing an insertion and removal sensor.

FIG. 4 is a diagram showing the insertion and removal sensor described above. a of FIG. 4 shows a proximal end portion (outer needle base) 154 of an outer needle, and b of FIG. 4 shows a proximal end portion (inner needle base) 153 of an inner needle. c of FIG. 4 shows a state in which the inner needle 152 is inserted into the inner cavity of the insertion needle body 151 forming the outer needle. On a surface of the outer needle base 154 facing the inner needle base 153 in the mounting state, a ring-shaped electrode (second electrode) 160 is provided (refer to a of FIG. 4). On the other hand, on a surface of the inner needle base 153 facing the outer needle base 154 in the mounting state, a pair of electrodes 161 and 162 are provided as the first electrode (refer to b of FIG. 4). When the inner needle 152 is inserted into the inner cavity of the insertion needle body 151 and the inner needle base 153 and the outer needle base 154 are brought into contact with each other, a pair of electrodes 161 and 162 provided in the inner needle base 153 and the electrode 160 provided in the outer needle base 154 are electrically connected to each other. For example, lead wires are attached to the electrodes 161 and 162, so that the pair of electrodes 161 and 162 are connected to the insertion and removal detection means 30. It is preferable that a pair of lead wires and the optical fiber 16 (refer to FIG. 1) are integrally sealed in a sheath outside the insertion needle 15. By checking whether or not the electrodes 161 and 162 are electrically connected to each other using the insertion and removal detection means 30, it is possible to determine whether or not the inner needle has been removed from the outer needle.

Figure 5:
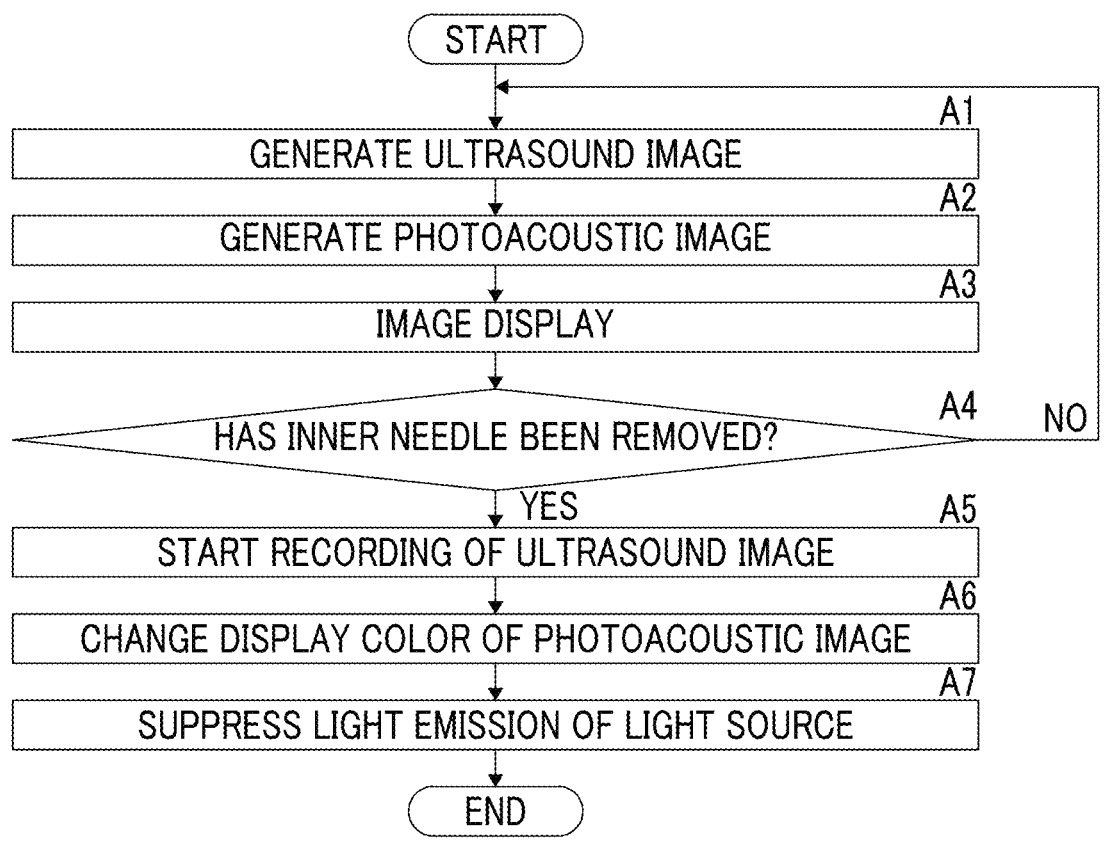
FIG. 5 is a flowchart showing the operation procedure of the photoacoustic image generation apparatus.

Subsequently, the operation procedure will be described. FIG. 5 shows the operation procedure of the photoacoustic image generation apparatus 10. The photoacoustic image generation apparatus 10 generates an ultrasound image (step A1). In this step, the control means 28 transmits an ultrasound trigger signal to the transmission control circuit 27. The transmission control circuit 27 makes the probe 11 transmit ultrasound waves in response to the ultrasound trigger signal. After the transmission of ultrasound waves, the probe 11 detects reflected ultrasound waves. The reflected ultrasound waves detected by the probe 11 are received by the receiving circuit 21, and the sampling data is stored in the receiving memory 22. The ultrasound image generation means 25 receives the sampling data of the detection signal of the reflected ultrasound waves through the data separation means 23, and generates an ultrasound image.

The photoacoustic image generation apparatus 10 generates a photoacoustic image (step A2). In this step, the control means 28 transmits a trigger signal to the laser unit 13. For example, a flash lamp trigger signal and a Q switch trigger signal are included in the trigger signal. In the laser unit 13, the flash lamp 52 (refer to FIG. 2) is turned on in response to the flash lamp trigger signal. Then, in response to the Q switch trigger signal, the Q switch 55 is driven to emit pulsed laser light. The pulsed laser light emitted from the laser unit 13 is guided to the vicinity of the distal end of the insertion needle 15 by the light guide member 155 (refer to FIG. 3), and is emitted from the light emitting portion 156. As a result, at least some of the pulsed laser light beams are emitted to the light absorption member 157 disposed at the distal end of the insertion needle 15. The probe 11 detects photoacoustic waves generated by the emission of the laser light, that is, photoacoustic waves emitted from the light absorption member 157. The photoacoustic waves detected by the probe are received by the receiving circuit 21, and the sampling data is stored in the receiving memory 22. The photoacoustic image generation means 24 receives the sampling data of the detection signal of the photoacoustic waves through the data separation means 23, and generates a photoacoustic image.

The image output means 26 displays the ultrasound image generated in step A1 and the photoacoustic image generated in step A2 on the image display means 14 (step A3). For example, the image output means 26 generates a composite image by superimposing the photoacoustic image on the ultrasound image, and outputs the composite image to the image display means 14. A doctor or the like inserts the insertion needle to a desired position while observing the composite image.

The insertion and removal detection means 30 determines whether or not the inner needle of the insertion needle 15 has been removed from the outer needle (step A4). When the inner needle 152 (refer to FIG. 3) is removed from the outer needle (insertion needle body) 151, the light guide member 155 and the light absorption member 157 are also removed from the insertion needle body 151 according to the removal. For this reason, it is thought that the level of the photoacoustic wave to be detected decreases abruptly. The insertion and removal detection means 30 determines that the inner needle has been removed from the outer needle, for example, when the pixel value in a photoacoustic image decreases abruptly and the state continues for one second or more. When it is determined that the inner needle has not been removed from the outer needle, the process returns to step A1 to continue the normal processing.

When the doctor or the like observes the image displayed on the image display means 14 to confirm that the distal end of the insertion needle 15 has been inserted to the desired position, the inner needle is removed from the outer needle to make preparation for injecting liquid, such as an anesthetic. When it is detected that the inner needle has been removed in step A4, the image recording means 32 starts the recording of an ultrasound image (step A5). The image recording means 32 starts the recording of an ultrasound image, for example, after a predetermined time has passed from the time when it is detected that the inner needle has been removed. This period may be set in consideration of a time required when a doctor or the like connects a syringe, for example.

When the recording of an ultrasound image is started, the image output means 26 may display "under recording" on the image display means 14. The photoacoustic image generation apparatus 10 continues to generate an ultrasound image. The doctor or the like may start the injection of anesthetic or the like after the recording of an ultrasound image is started.

When it is detected that the inner needle has been removed in step A4, the processing switching means 31 changes the display color of the photoacoustic image, which is displayed on the image display means 14 so as to be superimposed on the ultrasound image, to a different display color from the image display before it is detected that the inner needle has been removed (step A6). The processing switching means 31 may change the display color of the photoacoustic image in a region in the vicinity of a portion where the distal end of the insertion needle 15 is present, for example, a region of the range of a radius of 2 cm from a position as the center where the distal end of the insertion needle 15 is present, in the entire photoacoustic image. For example, the processing switching means 31 may display the photoacoustic image in red before it is detected that the inner needle has been removed, and may display the photoacoustic image in green after it is detected that the inner needle has been removed.

It is preferable that the photoacoustic image displayed in step A6 is an image at the time before it is detected that the inner needle has been removed, in particular, an image immediately before the time before it is detected that the inner needle has been removed. Normally, drug injection is performed with the position of the insertion needle fixed. Accordingly, a photoacoustic image generated immediately before the inner needle is removed is useful as an image showing a position where the drug is injected. At this time, since the display color has changed, the doctor or the like can easily recognize that the displayed photoacoustic image was generated in the past instead of real time.

When it is detected that the inner needle has been removed in step A4, the light source control means 33 suppresses the light emission of the laser unit 13 (step A7). For example, the light source control means 33 instructs the control means 28 to stop the transmission of a trigger signal to the laser unit 13. Since the trigger signal is not output to the laser unit 13, light emission of the laser unit 13 is stopped. Instead of stopping light emission, the pulse interval when the laser unit 13 emits pulsed laser light may be set to be longer than the pulse interval before it is detected that the inner needle has been removed. Alternatively, the intensity (power) of light emitted from the laser unit 13 may be set to be lower than the intensity of light before it is detected that the inner needle has been removed.

In the present embodiment, when it is detected that the inner needle has been removed, the processing switching means 31 changes the image display so as to be different from that before the inner needle is removed. If the inner needle is removed, the light guide member 155 and the light absorption member 157 are removed from the insertion needle body 151. Therefore, it is not possible to check the distal end position of the insertion needle 15 using a photoacoustic image. After the inner needle is removed, it is possible to check the position of the insertion needle 15 by displaying the photoacoustic image generated at the time before the inner needle is removed. At this time, the doctor or the like can easily recognize that the displayed photoacoustic image is a real time image by changing the display color of the photoacoustic image to that before it is detected that the inner needle has been removed.

In the present embodiment, the image recording means 32 starts the recording of an ultrasound image when it is detected that the inner needle has been removed. Particularly when injecting an anesthetic, the spreading of light leads to the block effect or the processing-related side effect. Accordingly, it is important to record how the liquid spreads. In the present embodiment, focusing on the fact that liquid injection is performed after the inner needle is removed, the recording of an ultrasound image is started when it is detected that the inner needle has been removed. In this manner, even if the doctor himself or herself who performs liquid injection does not perform a special operation for image recording, it is possible to record an ultrasound image.

In the present embodiment, the light source control means 33 suppresses the light emission of the laser unit 13 when it is detected that the inner needle has been removed. After the inner needle is removed, photoacoustic waves emitted from the light absorption member 157 cannot be detected by the probe 11. Therefore, it is not necessary to emit laser light. In particular, in a portable device, there is a demand to reduce power consumption associated with unnecessary light source driving as much as possible. In the present embodiment, since light emission is suppressed when it is detected that the inner needle has been removed, it is possible to suppress useless power consumption. In the present embodiment, the doctor or the like does not need to perform an operation for suppressing the light emission of the laser unit 13, it is possible to concentrate on liquid injection after removing the inner needle.

Figure 6:
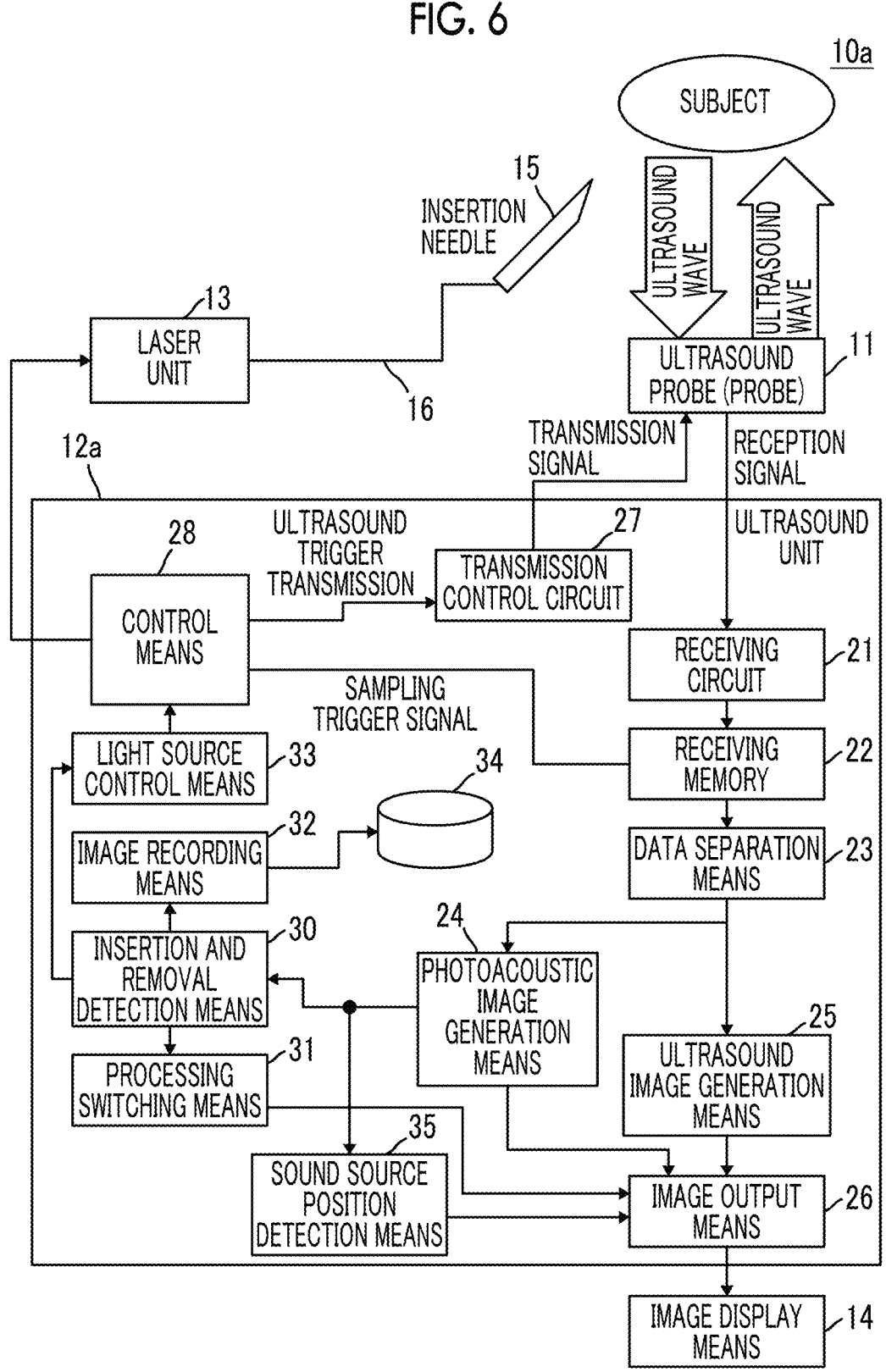
FIG. 6 is a block diagram showing a photoacoustic image generation apparatus according to a second embodiment of the present invention.

Next, a photoacoustic image generation apparatus of a second embodiment of the present invention will be described. FIG. 6 shows the photoacoustic image generation apparatus according to the second embodiment of the present invention. A photoacoustic image generation apparatus 10a according to the present embodiment is different from the photoacoustic image generation apparatus 10 according to the first embodiment shown in FIG. 1 in that sound source position detection means 35 for detecting the position of a photoacoustic wave generation source is added to an ultrasound unit 12a. In the present embodiment, the position of the photoacoustic wave generation source detected by the sound source position detection means 35 is displayed on the image display means 14. Others may be the same as in the first embodiment.

The sound source position detection means 35 detects the position of the photoacoustic wave generating source from the photoacoustic image generated by the photoacoustic image generation means 24. For example, the sound source position detection means 35 detects a position of a pixel having a maximum pixel value in the photoacoustic image as the position of the photoacoustic wave generating source. The position of the photoacoustic wave generating source corresponds to the position of the light absorption member 157 (refer to FIG. 3) of the insertion needle 15. The sound source position detection means 35 may detect the position of the photoacoustic wave generating source at a position deeper than the depth position set in advance. For example, the sound source position detection means 35 excludes a shallow region where the depth position is shallower than 2 mm, and detects the position of the photoacoustic wave generating source in a region where the depth position is 2 mm or more. This is because it is thought that the insertion needle 15 is not inserted into such a shallow region and the influence of artifacts is large at the shallow position and accordingly it is not possible to correctly detect the position of the photoacoustic wave generating source.

Figure 7:
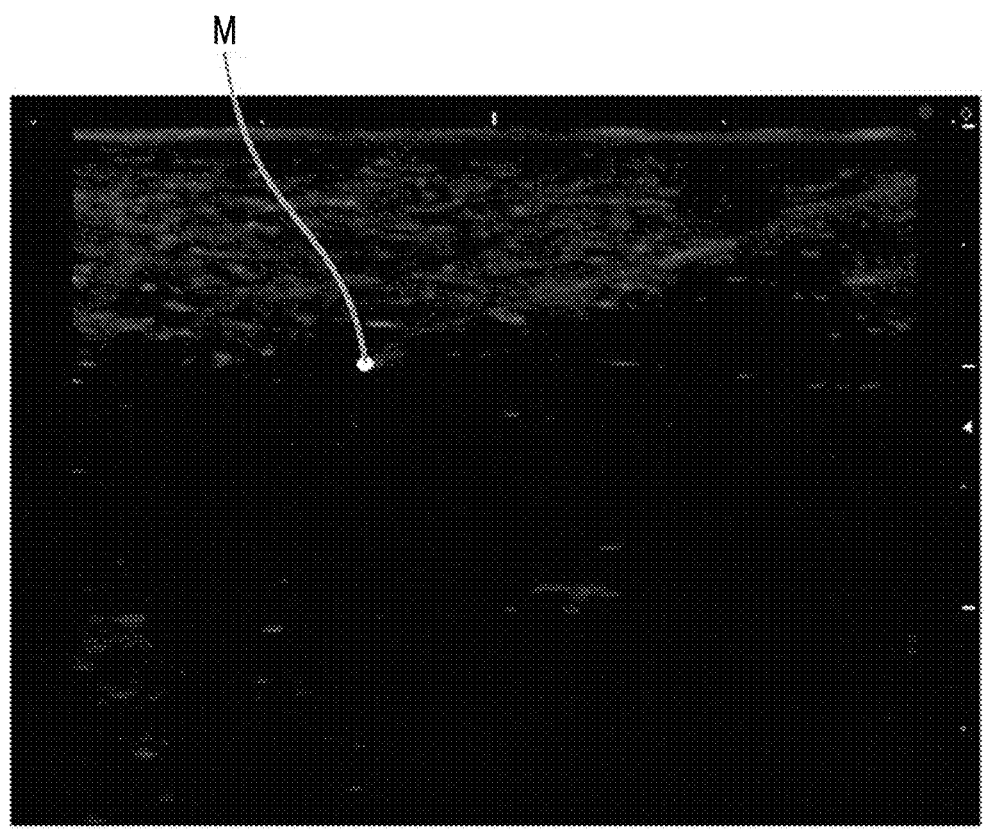
FIG. 7 is a diagram showing an example of a display image.

The sound source position detection means 35 transmits a signal (information), which indicates the position of the photoacoustic wave generation source, to the image output means 26. The image output means 26 displays a marker, which indicates the position of the photoacoustic wave generation source, on the image display means 14. FIG. 7 shows an example of a display image. The image output means 26 displays a marker M, which indicates the position of the photoacoustic wave generation source, so as to be superimposed on the ultrasound image, for example. The image output means 26 may display the marker M so as to be superimposed on a composite image obtained by superimposing the photoacoustic image on the ultrasound image. Through the marker M, it is possible to easily check the distal end position of the insertion needle 15. The image output means 26 may display the marker M so as to be superimposed on the composite image obtained by superimposing the photoacoustic image on the ultrasound image before it is detected that the inner needle has been removed, and may superimpose the marker M on a position immediately before the inner needle is removed on the ultrasound image after it is detected that the inner needle has been removed.

The processing switching means 31 changes the display color of the marker M displayed on the image display means 14 before and after it is detected that the inner needle has been removed. For example, the processing switching means 31 may display the marker M in red before it is detected that the inner needle has been removed, and may display the marker M in green after it is detected that the inner needle has been removed. The marker M may have any shape without being limited to the circular shape. In addition, the marker M is not limited to indicating the position of the photoacoustic wave generation source, that is, the position of the distal end portion of the insertion needle 15, as a point. For example, the detected position of the photoacoustic wave generation source may be surrounded by a rectangle, and a position where the distal end portion of the insertion needle is present may be indicated as a region.

In the present embodiment, the sound source position detection means 35 detects the position of the photoacoustic wave generation source based on the photoacoustic image, and displays a marker indicating the position of the photoacoustic wave generation source on the image display means 14. The doctor or the like can check the position of the distal end of the insertion needle 15 by observing the marker displayed on the image display means. Other effects are the same as in the first embodiment.

In the present embodiment, the sound source position detection means 35 may transmit a signal (information) indicating the position of the photoacoustic wave generation source to the insertion and removal detection means 30. Using the information received from the sound source position detection means 35, the insertion and removal detection means 30 may determine whether or not the inner needle has been removed from the outer needle based on the pixel value of the photoacoustic image in the vicinity of the position of the photoacoustic wave generation source.

Figure 8:
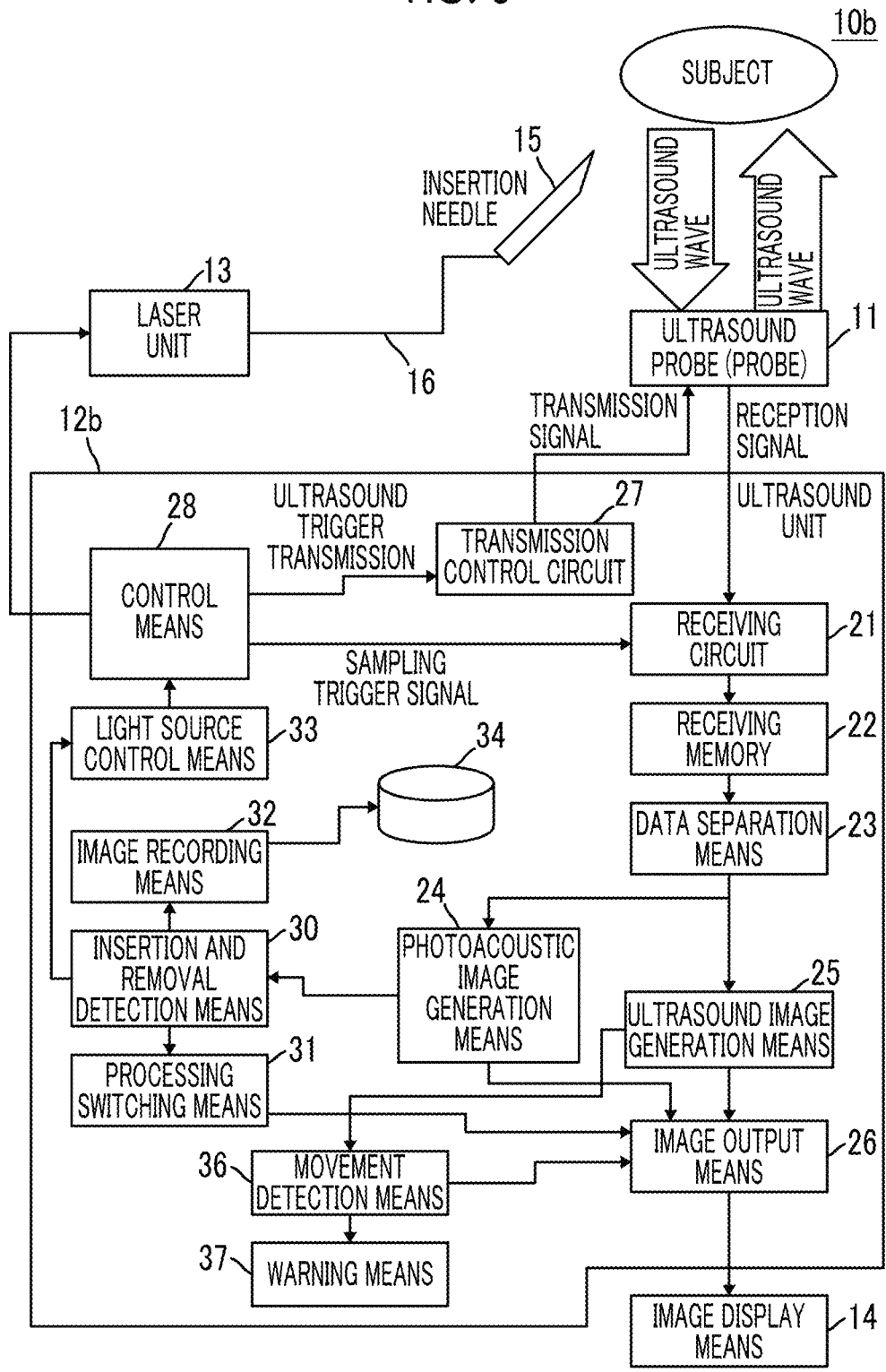
FIG. 8 is a block diagram showing a photoacoustic image generation apparatus according to a third embodiment of the present invention.

Subsequently, a third embodiment of the present invention will be described. FIG. 8 shows a photoacoustic image generation apparatus according to the third embodiment of the present invention. A photoacoustic image generation apparatus 10b according to the present embodiment is different from the photoacoustic image generation apparatus 10 according to the first embodiment shown in FIG. 1 in that movement detection means 36 and warning means 37 are added to an ultrasound unit 12b. Others may be the same as in the first embodiment. In addition, similar to the photoacoustic image generation apparatus 10a according to the second embodiment shown in FIG. 6, the photoacoustic image generation apparatus 10b according to the present embodiment may have the sound source position detection means 35.

The movement detection means 36 monitors the movement of the insertion needle 15, particularly the movement of the needle tip. After the insertion and removal detection means 30 detects that the inner needle has been removed from the outer needle, the movement detection means 36 detects the movement of the insertion needle 15 based on the ultrasound image at the time before it is detected that the inner needle has been removed and the ultrasound image at the current time. It is preferable that the ultrasound image at the time before it is detected that the inner needle has been removed is an ultrasound image at the time immediately before it is detected that the inner needle has been removed. The movement detection means 36 detects the movement of the needle tip of the insertion needle 15, for example, based on the difference between the total value of the pixel values in the ultrasound image generated at the time immediately before it is detected that the inner needle has been removed and the total value of the pixel values in the ultrasound image at the current time. For example, the movement detection means 36 calculates the total value of the pixel values of a region including a position where the photoacoustic wave generation source is present in a photoacoustic image, that is, a position where the light absorption member 157 (refer to FIG. 3) is present.

In a case where the needle tip of the insertion needle 15 does not move before and after the inner needle is removed, the pixel value of each pixel in the vicinity of the distal end of the insertion needle 15 in the ultrasound image shows the same value before and after the inner needle is removed. Accordingly, the difference between the total values of pixel values is small. On the other hand, when the insertion needle 15 moves after the inner needle is removed, a variation in the pixel value is large and the difference between the total values of pixel values is large since the insertion needle 15, which is a high reflector, moves in the ultrasound image. Therefore, it is possible to detect the movement of the insertion needle 15 by comparing the total value of the pixel values in the ultrasound image before the inner needle is removed with the total value of the pixel values in the ultrasound image at the current time. The difference between the total values of pixel values corresponds to the amount of movement that is detected.

The warning means 37 warns the user when the amount of movement detected by the movement detection means 36 becomes equal to or greater than the threshold value. As examples of the warning, an alarm or a warning display on the image display means 14 can be considered. For example, when the amount of movement detected by the movement detection means 36 is equal to or greater than a threshold value, the image output means 26 may change the display color of the photoacoustic image so as to be different from the display color before the detected amount of movement reaches the threshold value or more. For example, when the amount of movement is the threshold value, the display color of the photoacoustic image is changed from green to yellow. The image output means 26 may return the display color of the photoacoustic image to the original color when the detected amount of movement becomes equal to or less than a threshold value. The threshold value when changing the display color may be different from the threshold value when returning the display color to the original color. When the marker M (refer to FIG. 7) described in the second embodiment is being displayed on the image display means 14, the display color of the marker M may be changed.

The image recording means 32 may stop the recording of the ultrasound image when the amount of movement detected by the movement detection means 36 becomes equal to or greater than a threshold value. The image recording means 32 resumes the recording of the ultrasound image when the detected amount of movement becomes the threshold value after the recording of the ultrasound image is stopped. The threshold value when stopping the recording may be different from the threshold value when resuming the recording. In addition, the threshold value relevant to stop/resumption of recording may be different from the threshold value relevant to the change of a display color.

Figure 9:
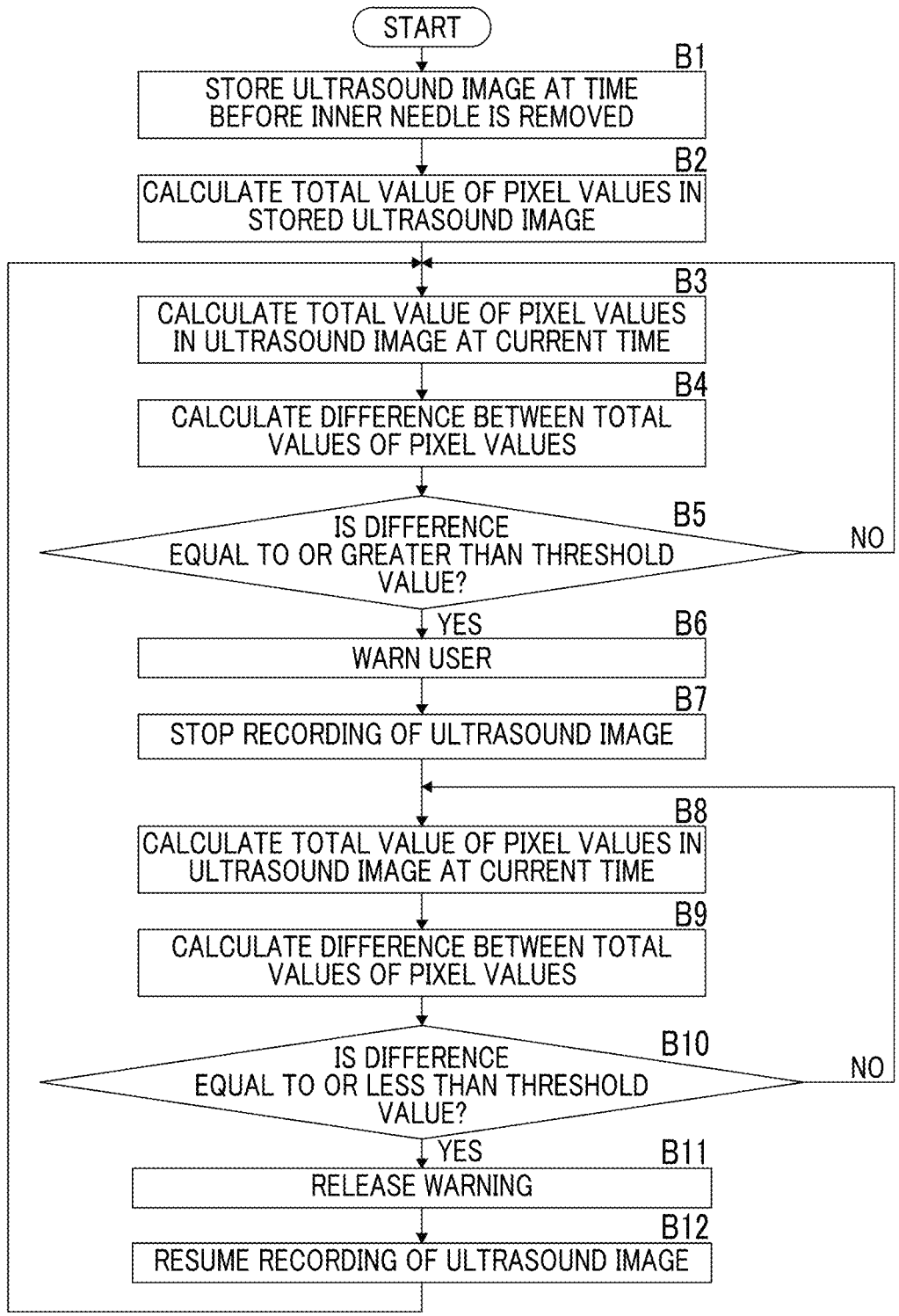
FIG. 9 is a flowchart showing an operation procedure after it is detected that an inner needle has been removed.

FIG. 9 shows an operation procedure after it is detected that the inner needle has been removed. This process is performed after it is detected that the inner needle has been removed in step A4 of FIG. 5. The movement detection means 36 stores an ultrasound image at the time before it is detected that the inner needle has been removed (step B1). The movement detection means 36 calculates the total value of the pixel values in the stored ultrasound image (step B2). For example, in a region of a range centered on a pixel corresponding to a position where the photoacoustic wave generation source is present in a photoacoustic image, the movement detection means 36 calculates the total value of the pixel values of pixels in the region. The shape of the region is not particularly limited, and may be a rectangle or a circle.

The movement detection means 36 calculates the total value of the pixel values in the ultrasound image at the current time (step B3). In step B3, the total value of the pixel values is calculated in the same region as the region for which the total value has been calculated in step B2. The movement detection means 36 calculates a difference between the total value of the pixel values calculated in step B2 and the total value of the pixel values calculated in step B3 (step B4). The movement detection means 36 determines whether or not the difference calculated in step B4 is equal to or greater than the threshold value (step B5). When the difference is less than the threshold value, since the needle tip has not moved, the process returns to step B3 to continue the monitoring of the movement of the needle tip.

When it is determined that the difference is equal to or greater than the threshold value in step B5, the warning means 37 notifies the user that the needle has moved, for example, by sounding an alarm or a buzzer (step B6). For example, the warning means 37 may display a message indicating that the needle tip has moved on the image display means 14 through the image output means 26. The image output means 26 may change the display color of the marker M or the photoacoustic image, which is displayed on the image display means 14, from green to yellow. The doctor or the like can see that the needle tip has moved by sound or image display. When it is determined that the difference is equal to or greater than the threshold value in step B5, the image recording means 32 stops the recording of the ultrasound image (step B7).

Ever after a warning is given to the user and the recording of the ultrasound image is stopped, the monitoring of the movement of the needle tip is continued. The movement detection means 36 calculates the total value of the pixel values in the ultrasound image at the current time (step B8), and calculates a difference between the total value of the pixel values calculated in step B2 and the total value of the pixel values calculated in step B8 (step B9). Steps B8 and B9 may be the same as steps B3 and B4, respectively. The movement detection means 36 determines whether or not the difference calculated in step B9 is equal to or less than the threshold value (step B10). When the difference is greater than the threshold value, since the needle tip has not returned to the position before the inner needle is removed, the process returns to step B8 to continue the monitoring of the movement of the needle tip. The threshold value in step B5 and the threshold value in step B10 may be the same value, or may be different values.

When it is determined that the difference is equal to or less than the threshold value in step B10, the warning means 37 releases the warning (step B11). The warning means 37 stops, for example, an alarm or a buzzer. In a case where a message indicating that the needle tip has moved is being displayed on the image display means 14, the display of the message is canceled. In the case of changing the display color of the photoacoustic image or the marker M displayed on the image display means 14, it is preferable to return the display color to the original color, for example, green. When it is determined that the difference is equal to or less than the threshold value in step B10, the image recording means 32 resumes the recording of the ultrasound image (step B12). Then, the process returns to step B3 to continue the monitoring of the movement of the needle tip.

In the present embodiment, the movement detection means 36 detects the movement of the insertion needle 15 based on the ultrasound image at the time before the inner needle is removed and the ultrasound image at the current time. When the insertion needle 15 moves, the pixel value in the ultrasound image changes. Therefore, by performing comparison with the ultrasound image at the time before the inner needle is removed, it is possible to determine whether or not the insertion needle 15 has moved from the position of the insertion needle 15 at that time. The warning means 37 warns the user when the detected amount of movement is equal to or greater than the threshold value. The user can see that the insertion needle 15 has moved by sound or image display, and can modify the position of the insertion needle 15 as necessary. Other effects are the same as those in the first embodiment.

Figure 10:
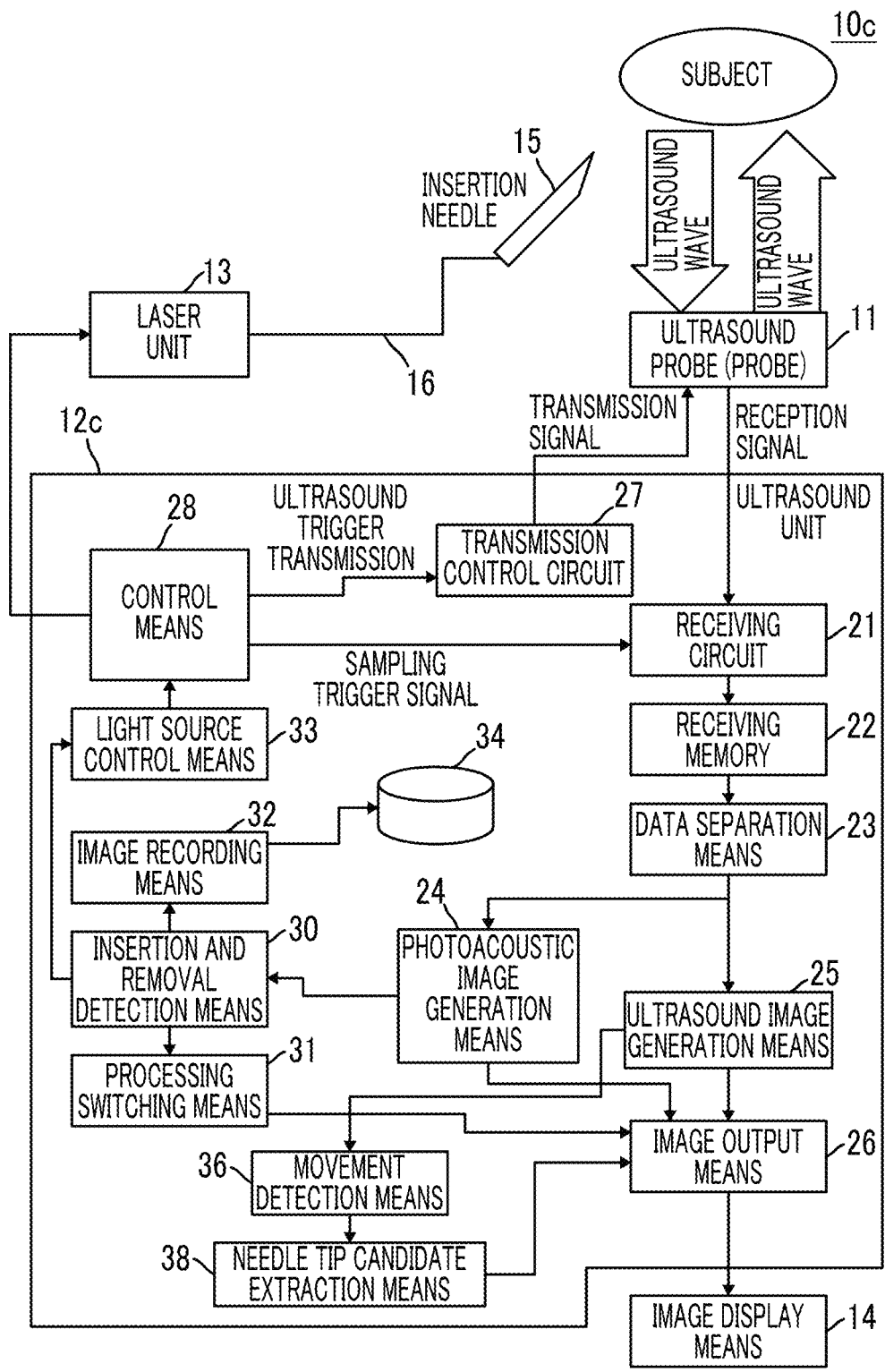
FIG. 10 is a block diagram showing a photoacoustic image generation apparatus according to a fourth embodiment of the present invention.

Subsequently, a fourth embodiment of the present invention will be described. FIG. 10 shows a photoacoustic image generation apparatus according to the fourth embodiment of the present invention. A photoacoustic image generation apparatus 10c of the present embodiment is different from the photoacoustic image generation apparatus 10 according to the first embodiment shown in FIG. 1 in that movement detection means 36 and needle tip candidate extraction means 38 are added to an ultrasound unit 12c. Others may be the same as in the first embodiment. In addition, the photoacoustic image generation apparatus 10c according to the present embodiment may have the sound source position detection means 35 similar to the photoacoustic image generation apparatus 10a according to the second embodiment shown in FIG. 6, or may have the warning means 37 similar to the photoacoustic image generation apparatus 10b according to the third embodiment shown in FIG. 8.

The movement detection means 36 is the same as that described in the third embodiment. The needle tip candidate extraction means 38 extracts a distal end candidate of the insertion needle 15 from the ultrasound image. The needle tip candidate extraction means 38 extracts the distal end candidate of the insertion needle 15, for example, when the amount of movement detected by the movement detection means 36 reaches a threshold value or more. The algorithm used when the needle tip candidate extraction means 38 extracts the needle tip candidate is not particularly limited. Techniques for extracting and tracking the needle tip from the ultrasound image are known, and are not directly related to the essence of the present invention. Accordingly, the detailed explanation thereof will be omitted.

In order to extract a needle tip candidate, for example, a method disclosed in JP2012-120747A can be used. Specifically, ultrasound waves are transmitted to a subject into which the insertion needle 15 has been inserted, and reflected waves (reflected ultrasound waves) of the ultrasound waves by the subject and the insertion needle 15 are received. Time-series echo signals of a plurality of frames are generated based on the received reflected ultrasound waves, and an ultrasound image is generated based on the generated time-series echo signals. By generating a difference echo signal (difference image) between time-series frames from the time-series echo signals of a plurality of frames and performing distal end detection processing based on the generated difference echo signal, one or more distal end candidates including the distal end portion of the insertion needle 15 are detected.

As disclosed in JP2012-120747A described above, in the needle tip candidate extraction processing, a distal end emphasis filter for emphasizing the needle tip portion in the ultrasound image can be used. As the distal end emphasis filter, it is possible to use a filter, which has a stepwise shape and in which pixels present in a direction in which the insertion needle is inserted are used for weighted addition, or a filter, which has a rectangular shape and in which weighted addition is performed with a large filter coefficient of each pixel present in the direction in which the insertion needle is inserted.

Figure 11:
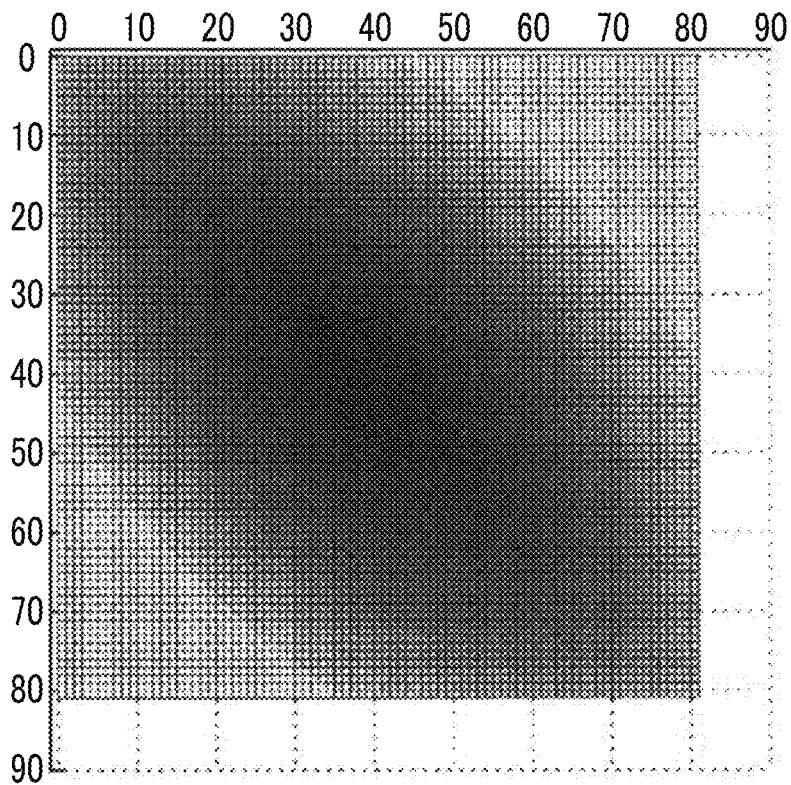
FIG. 11 is a diagram showing an example of a distal end emphasis filter.

FIG. 11 shows an example of the distal end emphasis filter. The distal end emphasis filter has a size of 81 vertical pixels by horizontal 81 pixels. The distal end emphasis filter is a filter that gives a weighting in the insertion direction of the insertion needle 15, has a size including the distal end portion of the insertion needle 15, and performs weighted addition with a large filter coefficient of each pixel present in the insertion direction. The filter coefficient of each pixel can be determined by applying a two-dimensional Gaussian function. In FIG. 11, the magnitude of the filter coefficient of the filter is expressed by density shading.

As shown in FIG. 11, in the distal end emphasis filter, the filter coefficient increases toward the center, and filter coefficients on the concentric ellipse centered on the center pixel are the same. The longitudinal direction of the ellipse matches the insertion direction of the insertion needle 15. The needle tip candidate extraction means 38 stores a plurality of distal end emphasis filters corresponding to the insertion angle of the insertion needle 15 and the size of the insertion needle 15 in a storage unit (not shown). The aspect ratio of the distal end emphasis filter is determined according to the insertion angle. According to the insertion angle of the insertion needle 15 or the size of the insertion needle 15 that is used, a distal end emphasis filter corresponding thereto is read. Then, for the difference image, distal end emphasis processing for performing weighted addition with respect to the surrounding pixels is performed using the distal end emphasis filter. By performing the distal end emphasis processing in the needle tip candidate extraction processing, it is possible to extract the distal end portion of the insertion needle 15 with higher accuracy.

The distal end emphasis processing described above can also be used for movement detection in the movement detection means 36. For the ultrasound image generated at the time before it is detected that the inner needle has been removed, the movement detection means 36 performs distal end emphasis processing for performing weighted addition with respect to the surrounding pixels using the distal end emphasis filter. The distal end emphasis processing is similarly performed for the ultrasound image at the current time. The movement detection means 36 may detect the movement of the insertion needle 15 by calculating a difference between the images having been subjected to the distal end emphasis processing. The point that the distal end emphasis processing may also be performed by the movement detection means 36 is the same as in the third embodiment.

When the amount of movement detected by the movement detection means 36 becomes equal to or greater than the threshold value, the image output means 26 displays a marker, which indicates the position of the distal end candidate of the insertion needle 15 extracted by the needle tip candidate extraction means, on the image display means 14. After the marker indicating the position of the distal end candidate of the insertion needle 15 is displayed on the image display means 14, the image output means 26 stops the display of the marker when the amount of movement detected by the movement detection means 36 becomes equal to or less than the threshold value.

Here, when the distal end of the insertion needle 15 moves in a deeper direction, the area of a portion occupied by the insertion needle 15 that is a high reflector increases in a region in the vicinity of the distal end of the insertion needle 15 of the ultrasound image. Therefore, in the movement detection means 36, when a value obtained by subtracting the total value of the ultrasound image at the current time from the total value of the pixel values of the ultrasound image before the inner needle is removed is calculated, the value (subtraction value) is a negative value. In addition, the absolute value of the subtraction value indicates the amount of movement.

On the other hand, when the insertion needle 15 moves in a shallower direction, the area of a portion occupied by the insertion needle 15 that is a high reflector decreases in a region in the vicinity of the distal end of the insertion needle 15 of the ultrasound image. Therefore, in the movement detection means 36, when a value obtained by subtracting the total value of the ultrasound image at the current time from the total value of the pixel values of the ultrasound image before the inner needle is removed is calculated, the value (subtraction value) is a positive value. Therefore, according to whether the subtraction value is a positive value or a negative value, it is possible to determine whether the distal end of the insertion needle 15 has moved in a deeper direction or in a shallower direction.

When the injection of a drug using the insertion needle 15 ends, the insertion needle 15 is removed from the subject. In other words, the distal end of the insertion needle 15 moves in a shallow direction. The movement detection means 36 can determine that the insertion needle 15 is moving in a direction in which the insertion needle 15 is removed when the subtraction value is a positive value. When the detected amount of movement (absolute value of the subtraction value) is equal to or greater than a predetermined amount and the subtraction value is a positive value, that is, when it is detected that the insertion needle 15 has moved in a direction in which the insertion needle 15 is removed by the predetermined amount or more, the movement detection means 36 may output a signal indicating that the insertion needle 15 has been removed to the image recording means 32 and the needle tip candidate extraction means 38. The image recording means 32 ends the recording of the ultrasound image when the signal indicating that the insertion needle 15 has been removed is input from the movement detection means 36. The needle tip candidate extraction means 38 ends the needle tip candidate extraction processing when the signal indicating that the insertion needle 15 has been removed is input from the movement detection means 36.

Figure 12:
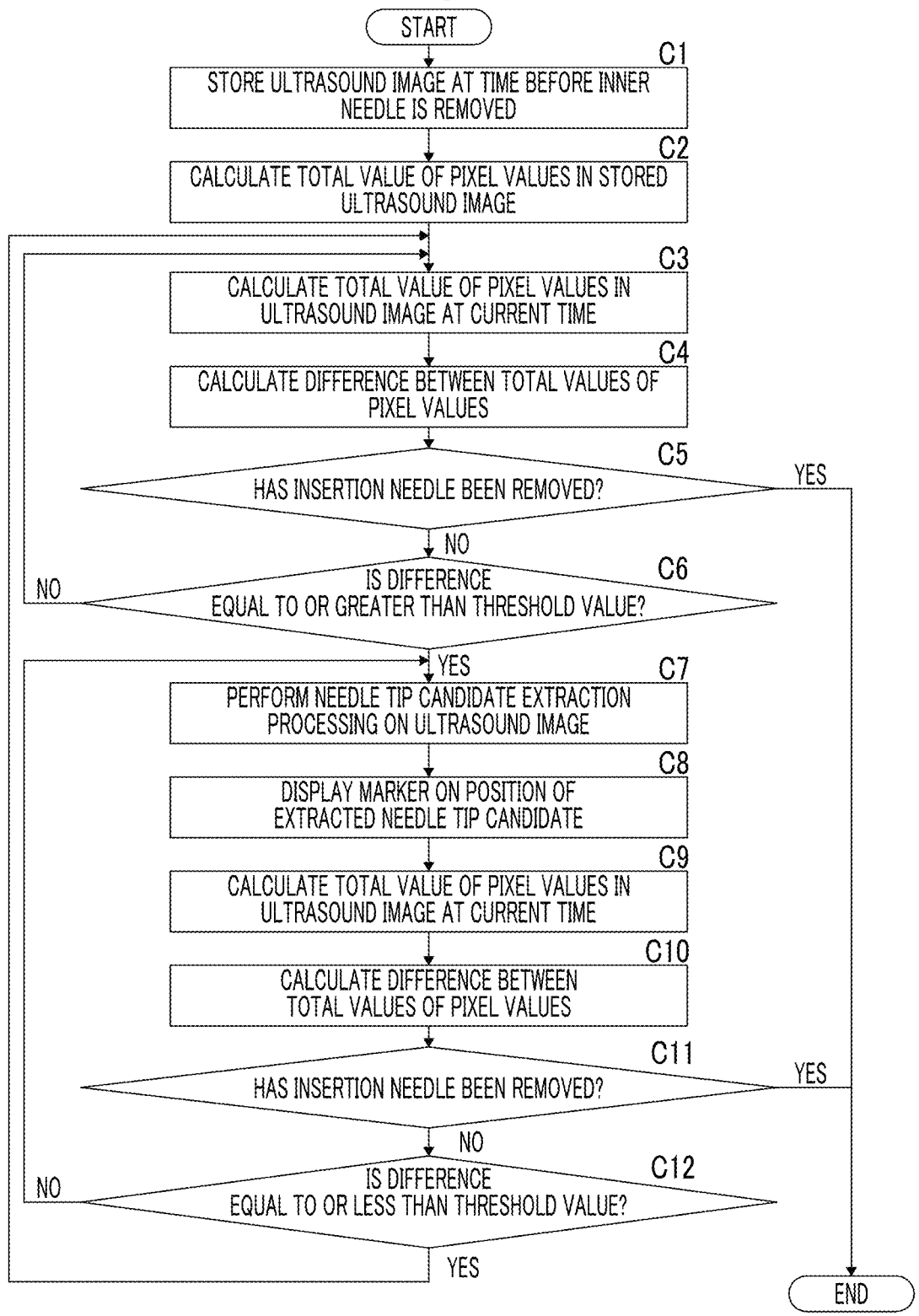
FIG. 12 is a flowchart showing an operation procedure after it is detected that an inner needle has been removed.

FIG. 12 shows an operation procedure after it is detected that the inner needle has been removed. This process is performed after it is detected that the inner needle has been removed in step A4 of FIG. 5. The movement detection means 36 stores an ultrasound image at the time before it is detected that the inner needle has been removed (step C1). The movement detection means 36 calculates the total value of the pixel values in the stored ultrasound image (step C2). For example, in a region of a range centered on a pixel corresponding to a position where the photoacoustic wave generation source is present in a photoacoustic image, the movement detection means 36 calculates the total value of the pixel values of pixels in the region.

The movement detection means 36 calculates the total value of the pixel values in the ultrasound image at the current time (step C3). In step C3, the total value of the pixel values is calculated in the same region as the region for which the total value has been calculated in step C2. The movement detection means 36 calculates a difference between the total value of the pixel values calculated in step C2 and the total value of the pixel values calculated in step C3 (step C4). The movement detection means 36 determines whether or not the inner needle has been removed based on the difference calculated in step C4 (step C5). The movement detection means 36 determines that the inner needle has been removed when the absolute value of a subtraction value, which is obtained by subtracting the total value of the pixel values calculated in step C3 from the total value of the pixel values calculated in step C2, is greater than a predetermined value and the subtraction value is a positive value. When it is determined that the inner needle has been removed, the process ends.

The movement detection means 36 determines whether or not the difference calculated in step C4 is equal to or greater than the threshold value (step C6). When the difference is less than the threshold value, since the needle tip has not moved, the process returns to step C3 to continue the monitoring of the movement of the needle tip. When it is determined that the difference is equal to or greater than the threshold value in step C4, the needle tip candidate extraction means 38 extracts a needle tip candidate from the ultrasound image (step C7). The image output means 26 displays a marker so as to be superimposed on the position of the extracted needle tip candidate in the ultrasound image (step C8). After the needle tip has moved, the doctor or the like can check the position of the moved needle tip by displaying the position of the needle tip extracted using the ultrasound image so as to be superimposed on the ultrasound image.

Then, the movement detection means 36 calculates the total value of the pixel values in the ultrasound image at the current time (step C9), and calculates a difference between the total value of pixel values calculated in step C2 and the total value of the pixel values calculated in step C9 (step C10). Steps C9 and C10 may be the same as steps C3 and C4, respectively. The movement detection means 36 determines whether or not the inner needle has been removed based on the difference calculated in step C10 (step C11). Step C11 may be the same as step C5. When it is determined that the inner needle has been removed, the process ends.

The movement detection means 36 determines whether or not the difference calculated in step C10 is equal to or less than the threshold value (step C12). When the difference is greater than the threshold value, since the needle tip has not returned to the position before the inner needle is removed, the process returns to step C7 to continue the needle tip candidate extraction processing. When it is determined that the difference is less than the threshold value in step C12, the process returns to step C3 to continue the monitoring of the movement of the needle tip. The threshold value in step C6 and the threshold value in step C12 may be the same value, or may be different values.

In the present embodiment, the needle tip candidate extraction means 38 extracts a distal end candidate of the insertion needle 15 from the ultrasound image. The image output means 26 performs image display, which shows a portion of the distal end candidate extracted by the needle tip candidate extraction means 38, when the amount of movement detected by the movement detection means 36 is large. When the position of the insertion needle 15 deviates greatly from the position when it is detected that the inner needle has been removed, the doctor or the like can check the current position of the insertion needle 15 by displaying the position of the distal end extracted using the ultrasound image. Accordingly, it is possible to return the position of the distal end of the insertion needle 15 to a desired insertion position. Other effects are the same as those in the first embodiment.

In addition, although the example in which the light guide member 155 is embedded into the tube 158 using the transparent resin 159 and the light absorption member 157 is disposed at the distal end of the transparent resin 159 has been described in FIG. 3, the present invention is not limited thereto. For example, a film having a light absorption property may be used as the light absorption member 157 to cover the light emitting portion 156, which is the light emitting surface of the light guide member 155, with the film having a light absorption property, and the light guide member 155 may be embedded into the transparent resin. Alternatively, a gap may be provided between the light emitting portion 156 of the light guide member 155 and the light absorption member 157, so that the light emitting portion 156 and the light absorption member 157 face each other with the air layer interposed therebetween.

In addition, although the example in which the inner needle 152 has the tube 158 has been described in FIG. 3, the present invention is not limited thereto. For example, an inner needle may be formed of a material having a light absorption property, for example, black resin, and the light guide member 155 may be embedded thereinside. In this case, the inner needle, in particular, the distal end portion of the inner needle also serves as the light absorption member 157 that absorbs light, which is emitted from the light emitting portion 156 of the light guide member 155, to generate an acoustic wave. Instead of embedding the light guide member 155 into the resin, the light guide member 155 having almost the same outer diameter as the inner diameter of the insertion needle body 151 may be used, and the light guide member 155 itself may be used as an inner needle. In this case, a film having a light absorption property, for example, a black fluorine resin may be used as the light absorption member 157, so that at least a part of the light guide member 155 including the light emitting portion 156 is covered by the black fluororesin.

The light absorption member 157 is not essential. For example, the light emitted from the light emitting portion 156 may be emitted to the insertion needle body 151, and a portion of the insertion needle body 151 to which light is emitted may become a photoacoustic wave generating portion and a photoacoustic wave may be generated from the portion. For example, a light emitting portion and a photoacoustic wave generating portion may be disposed in the vicinity of the distal end of the insertion needle 15, so that the photoacoustic wave is generated in the vicinity of the distal end of the insertion needle 15. The "vicinity" of the distal end of the insertion needle 15 referred to herein means a position where it is possible to generate photoacoustic waves capable of imaging the position of the distal end of the insertion needle 15 with accuracy, which is required for insertion work, in a case where the light emitting portion and the photoacoustic wave generating portion are disposed at the position. For example, "vicinity" indicates the range of 0 mm to 3 mm toward the proximal end side from the distal end of the insertion needle 15.

The insertion needle 15 is not limited to being percutaneously inserted into the subject from the outside of the subject, and a needle for ultrasound endoscope may be used. The light guide member 155 and the light absorption member 157 may be provided in the needle for ultrasound endoscope, light may be emitted to the light absorption member 157 provided in the distal end portion of the needle, and photoacoustic waves may be detected to generate a photoacoustic image. In this case, it is possible to insert the needle for ultrasound endoscope while checking the position of the distal end portion of the needle for ultrasound endoscope by observing the photoacoustic image. The photoacoustic wave generated in the distal end portion of the needle for ultrasound endoscope may be detected using a probe for body surface, or may be detected using a probe built into the endoscope.

Although the needle having an opening at the distal end is assumed as a needle in the embodiment described above, the opening does not necessarily need to be provided in the distal end portion. The needle is not limited to a needle, such as an injection needle, and may be a biopsy needle used for a biopsy. That is, a biopsy needle that can be inserted into the inspection target of the body in order to sample the tissue in the inspection target may be used. In this case, photoacoustic waves may be generated in a sampling portion (inlet port) for sampling the tissue of a biopsy part by sucking the tissue.

In FIG. 1, only one insertion needle 15 is drawn. However, the number of inserts to be imaged in a photoacoustic image is not limited to one. A plurality of sets of inserts and laser units corresponding thereto may be prepared, and a photoacoustic image may be generated for each insert so that the position of each insert can be checked through the photoacoustic image. During image display, the color of a photoacoustic image may be changed for each insert, and the photoacoustic image with the changed color may be superimposed on the ultrasound image. In this case, it is possible to distinguish between a plurality of inserts in the image.

Figure 13:
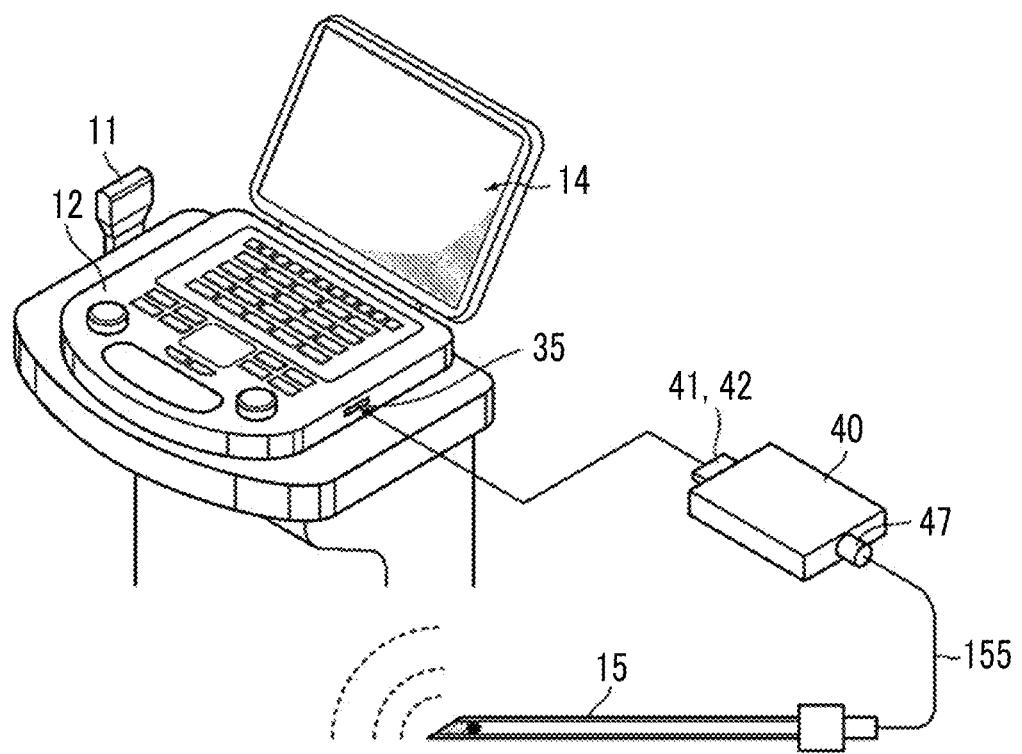
FIG. 13 is a diagram showing the appearance of a photoacoustic image generation apparatus.

Finally, FIG. 13 shows the appearance of a photoacoustic image generation apparatus. The probe 11 is connected to the ultrasound unit 12. The ultrasound unit 12 is configured as an integrated device including the image display means 14. The ultrasound unit 12 typically has a processor, a memory, a bus, and the like. A program regarding photoacoustic image generation is installed in the ultrasound unit 12.

The ultrasound unit 12 has a USB port 40. A USB connector including a power input terminal 41 and a trigger input terminal 42 of a laser unit 13 is inserted into the USB port 40. In a case where the laser unit 13 is a card-sized small and lightweight device, it is possible to hold the USB connector by inserting the USB connector into the USB port of the ultrasound unit 12. The USB port 40 may have any shape allowing a normal USB connector to be inserted thereinto, and does not need to be a port for transmitting and receiving a signal conforming to the normal USB standard. In the USB port, a signal line for a trigger signal may be included instead of a digital signal line. That is, the USB port 40 may be a USB type port as a connector having a total of four terminals of two lines for power supply and two lines for triggering. By using the signal line for a trigger signal instead of the digital signal line, it becomes easy to take trigger synchronization with the laser unit 13.

One end of the optical fiber that forms the light guide member 155 (refer to FIG. 3) of the insertion needle 15 is connected to a light output terminal 47 of the laser unit 13. The optical fiber is inserted into the light output terminal 47, and is held by spring force or the like. If the operator applies a strong force to the light output terminal 47, for example, by pulling the insertion needle 15, the optical fiber exits from the light output terminal 47. Accordingly, it is possible to prevent the optical fiber from being broken. In addition, by making it possible to directly insert or remove the optical fiber into or from the light output terminal 47, there is an effect that the cost can be reduced without providing a connector in the optical fiber extending from the insertion needle 15.

Pulse energy of the pulsed laser light output from the laser unit 13 can be set to 6.4 µJ if the core diameter of the optical fiber forming the light guide member 155 is 200 µm. The pulse energy of the pulsed laser light can be set to 2.0 µJ if the core diameter of the optical fiber is 100 µm. The pulse time width can be set to 80 ns.

In FIG. 13, the light output terminal 47 is provided on a surface opposite to a surface on which the USB connector including the power input terminal 41 and the trigger input terminal 42 is present. However, it is preferable that the light output terminal 47 is provided on a surface perpendicular to the surface on which the USB connector is present. In a case where the USB connector and the light output terminal 47 are provided on the opposite surfaces, if the laser unit 13 is pulled when the operator moves the insertion needle 15, the USB connector may exit from the USB port 40. In contrast, in a case where the USB connector and the light output terminal 47 are provided on the surfaces perpendicular to each other, the USB connector is difficult to exit from the USB port 40 even if the laser unit 13 is pulled.

In FIG. 13, the laser unit 13 is directly connected to the USB port 40. However, the present invention is not limited thereto, and the USB port 40 and the laser unit 13 may be connected to each other using an extension cable or the like. The trigger input terminal 42 does not need to be included in the USB connector, and the laser unit 13 may acquire a trigger signal from a connector (terminal) different from the USB port 40. For example, a trigger signal may be acquired from a connector for electrocardiogram (ECG) measurement attached to the normal ultrasound system. Alternatively, a trigger signal may be acquired from some terminals of the connector of the probe.

While the present invention has been described based on the preferred embodiment, the photoacoustic image generation apparatus, the signal processing device, and the photoacoustic image generation method of the present invention are not limited to the above embodiment, and various modifications and changes in the configuration of the above embodiment are also included in the range of the present invention.

What is claimed is:

1. A photoacoustic image generation apparatus, comprising:
   an insertion needle that has an outer needle having an inner cavity and an inner needle removably inserted into the inner cavity of the outer needle, the inner needle including a light emitting portion that emits light guided from a light source and a photoacoustic wave generating portion that absorbs the light emitted from the light emitting portion to generate photoacoustic waves;
   acoustic wave detection unit for detecting the photoacoustic waves emitted from the photoacoustic wave generating portion;
   photoacoustic image generation unit for generating a photoacoustic image based on the detected photoacoustic waves;
   image output unit for displaying the photoacoustic image on image display unit;
   insertion and removal detection unit for detecting that the inner needle has been removed from the outer needle; and
   processing switching unit for changing image display so as to be different from image display before it is detected that the inner needle has been removed in a case where it is detected that the inner needle has been removed.

2. The photoacoustic image generation apparatus according to claim 1, wherein the insertion needle is configured to be insertable into a subject in a state in which the inner needle has been inserted into the outer needle.

3. The photoacoustic image generation apparatus according to claim 1,
   wherein the processing switching unit changes a display color of the photoacoustic image displayed on the image display unit before and after it is detected that the inner needle has been removed.

4. The photoacoustic image generation apparatus according to claim 1, further comprising:
   a sound source position detection unit for detecting a position of a generation source of the photoacoustic waves in the insertion needle based on the photoacoustic image,
   wherein the image output unit displays a marker indicating the detected position of the generation source of the photoacoustic waves on the image display unit, and
   the processing switching unit changes a display color of the marker displayed on the image display unit before and after it is detected that the inner needle has been removed.

5. The photoacoustic image generation apparatus according to claim 1,
   wherein the acoustic wave detection unit further detects reflected acoustic waves of acoustic waves transmitted into a subject, and
   reflected acoustic wave image generation unit for generating a reflected acoustic wave image based on the detected reflected acoustic waves is further provided.

6. The photoacoustic image generation apparatus according to claim 5,
   wherein the image output unit displays an image, in which the photoacoustic image is superimposed on the reflected acoustic wave image, on the image display unit before it is detected that the inner needle has been removed, and displays the reflected acoustic wave image on the image display unit after it is detected that the inner needle has been removed.

7. The photoacoustic image generation apparatus according to claim 6,
   wherein the image output unit displays an image, in which a photoacoustic image generated before it is detected that the inner needle has been removed is superimposed on the reflected acoustic wave image, on the image display unit after it is detected that the inner needle has been removed.

8. The photoacoustic image generation apparatus according to claim 5, further comprising:
   movement detection unit for detecting a movement of the insertion needle based on a reflected acoustic wave image at a time before it is detected that the inner needle has been removed and a reflected acoustic wave image at a current time after it is detected that the inner needle has been removed.

9. The photoacoustic image generation apparatus according to claim 8,
   wherein the movement detection unit detects a movement of a needle tip of the insertion needle based on a difference between a total value of pixel values in the reflected acoustic wave image at the time before it is detected that the inner needle has been removed and a total value of pixel values in the reflected acoustic wave image at the current time.

10. The photoacoustic image generation apparatus according to claim 9,
    wherein the movement detection unit calculates the total values of the pixel values after performing distal end emphasis processing, which is for emphasizing a distal end portion of the insertion needle, for each of the reflected acoustic wave image at the time before it is detected that the inner needle has been removed and the reflected acoustic wave image at the current time.

11. The photoacoustic image generation apparatus according to claim 9,
wherein the movement detection unit calculates a total value of pixel values in a region including a position of the photoacoustic wave generating portion in the photoacoustic image.

12. The photoacoustic image generation apparatus according to claim 8, further comprising:
warning unit for warning a user in a case where an amount of movement detected by the movement detection unit is equal to or greater than a threshold value.

13. The photoacoustic image generation apparatus according to claim 8,
wherein, in a case where an amount of movement detected by the movement detection unit is equal to or greater than a threshold value, the image output unit changes a display color of the photoacoustic image to a different display color from a display color before the amount of movement detected by the movement detection unit reaches the threshold value or more.

14. The photoacoustic image generation apparatus according to claim 13,
wherein, when the amount of movement detected by the movement detection unit becomes smaller than the threshold value after the amount of movement reaches the threshold value or more, the image output unit returns the display color of the photoacoustic image to the display color before the amount of movement reaches the threshold value or more.

15. The photoacoustic image generation apparatus according to claim 8, further comprising:
needle distal end extraction unit for extracting a distal end candidate of the insertion needle from the reflected acoustic image,
wherein the image output unit displays a marker, which indicates a position of a distal end candidate of the insertion needle extracted by the needle tip candidate extraction unit, on the image display unit in a case where an amount of movement detected by the movement detection unit is equal to or greater than a threshold value.

16. The photoacoustic image generation apparatus according to claim 15,
wherein the image output unit stops the display of the marker when the amount of movement detected by the movement detection unit becomes smaller than the threshold value after the amount of movement reaches the threshold value or more.

17. The photoacoustic image generation apparatus according to claim 15,
wherein the needle tip candidate extraction unit ends the needle tip candidate extraction processing in a case where the movement detection unit detects that the insertion needle has moved by a predetermined amount or more in a direction in which the insertion needle is removed.

* * * * *